(12) United States Patent
Kmiec et al.

(10) Patent No.: US 7,807,648 B2
(45) Date of Patent: Oct. 5, 2010

(54) G-RICH POLYNUCLEOTIDES FOR THE TREATMENT OF HUNTINGTON'S DISEASE

(75) Inventors: Eric B. Kmiec, Landenberg, PA (US); Hetal Parekh-Olmedo, Mickleton, NJ (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 11/544,278

(22) Filed: Oct. 6, 2006

(65) Prior Publication Data

US 2007/0105805 A1    May 10, 2007

Related U.S. Application Data

(60) Provisional application No. 60/724,085, filed on Oct. 6, 2005.

(51) Int. Cl.
*A61K 48/00* (2006.01)
*C07H 21/04* (2006.01)

(52) U.S. Cl. .................................. 514/44; 536/235
(58) Field of Classification Search ................ None
See application file for complete search history.

(56) References Cited

U.S. PATENT DOCUMENTS 4,683,202 A    7/1987 Mullis

FOREIGN PATENT DOCUMENTS

WO    WO97/03997    *    6/1997

OTHER PUBLICATIONS

Harper et al. PNAS. Apr. 19, 2005. vol. 102; No. 16: pp. 5820-5825.*
Pisetsky et al (Immunopharmacology 40(1998) 199-208).*
Evert et al. Cell and Tissue Research. Jun. 2000; 301(1): 189-204.*
Skogen et al. (BCM Neuroscience 2006, 7(65): 1-16).*
Dapić et al. (Nucleic Acids Research. 2003; 31(8): 2097-2107).*
Jeffers et al. (Expert Opin. Ther. Targets. 2002; 6(4): 469-482).*
Patil et al. (The AAPS Journal. 2005; 7(1) Article 9: E61-E77).*
Biyani, M., et al. "Structural Characterization of Ultra-Stable Higher-Ordered Aggregates Generated By Novel Guanine-Rich DNA Sequences"; Gene 364 (2005); pp. 130-138.
Bates, Paula J., et al. "Antiproliferative Activity of G-rich Oligonucleotides Correlates with Protein Binding"; The Journal of Biological Chemistry; vol. 274, No. 37, Sep. 10, 1999; pp. 26369-26377.
Dapic, V., et al. Antiproliferative Activity of G-Quartet-Forming Oligonucleotides with Backbone and Sugar Modifications; Biochemistry 2002, 41; pp. 3676-3685.
Xu, X., et al., "Inhibition of DNA Replication and Induction of S Phase Cell Cycle Arrest by G-rich Oligonucleotides"; The Journal of Biological Chemistry; vol. 276, No. 46, Nov. 16, 2001; pp. 43221-43230.

* cited by examiner

*Primary Examiner*—Scott Long
(74) *Attorney, Agent, or Firm*—McCarter & English

(57) ABSTRACT

The present invention relates to oligonucleotide compositions and therapeutic uses thereof to modify protein-protein interactions. In particular, the invention relates to the use of a guanidine-rich oligonucleotides to disrupt disease-causing protein aggregates, for example, Huntington's Disease (HD) protein aggregates.

4 Claims, 14 Drawing Sheets

G-RICH POLYNUCLEOTIDES FOR THE TREATMENT OF HUNTINGTON'S DISEASE

CROSS-REFERENCE TO RELATED APPLICATIONS

This application is entitled under 35 U.S.C. §119(e) to claim the benefit of U.S. Provisional Patent Application No. 60/724,085, filed Oct. 6, 2005, entitled: G-Rich Polynucleotides as a Novel Therapeutic for the Treatment of Huntington's Disease, the disclosure of which is hereby incorporated by reference in its entirety.

INCORPORATION BY REFERENCE OF SEQUENCE LISTING

The present application hereby incorporates by reference, in its entirety, the Sequence Listing, and identical CRF of the Sequence Listing filed herewith. The CRF contains nucleic acid sequences, SEQ. ID NO. 1-7, in file: "GRO_Kmiec.txt;" created: Oct. 4, 2006; OS: MS Windows XP; Software: PatentIn 3.3; size: 6 KB. The information contained in the Sequence Listing submitted, herewith, in the instant application is identical to the sequence information contained in the computer readable form.

FIELD OF THE INVENTION

The present invention relates to oligonucleotide compositions and methods of use thereof to modify protein-protein interactions. In particular, the invention relates to the use of a guanidine-rich oligonucleotides to disrupt disease-causing protein aggregates, for example, Huntington's Disease (HD) protein aggregates.

BACKGROUND OF THE INVENTION

Huntington's Disease (HD) is an inherited autosomal dominant genetic disorder caused by expansions of CAG repeats (polyglutamine-polyQ) at the N-terminus, within exon 1, of the HD protein. HD is marked by neuronal tissue degeneration and appears be due to the development of protein aggregates that arise initially from the misfolding of the mutant HD protein. Recent studies suggest that mutant Htt can nucleate protein aggregation and interfere with a multitude of normal cellular functions. protein. Recent studies suggest that mutant Htt can nucleate protein aggregation and interfere with a multitude of normal cellular functions.

The extent of polyglutamine expansion is correlated with the severity of the symptoms and their onset while the pathology of the disease and neuronal cell death are thought to be associated with protein misfolding and protein aggregation. These aggregates are usually seen in the nucleus but can also be found in the cytoplasm. Protein aggregates develop via a complex biochemical process with intermediates being visible during the process. PolyQ tracts within the pathogenic range induce a protein insolubility whereas Htt with non-pathogenic length maintains a measured degree of solubility.

Consistent with the aggregate toxicity hypothesis, inhibition of aggregate formation has been shown to have beneficial effects on the progression of HD in the R6/2 mouse model. The implication of the polyQ aggregates in cytotoxicity validates them as targets for novel therapeutics. Despite the lack of details surrounding the molecular structure of the polyQ aggregates, high throughput screening for compounds that inhibit their formation have produced some promising results. Several compounds, including Congo Red and Clioquinol, have been reported to inhibit the aggregation process in the R6/2 mouse model but their neurotoxicity tempers enthusiasm. Thus, identifying molecules that show efficacy with minimal toxicity should be an important consideration in the search for HD therapeutics.

Synthetic ODNs (ODNs) provide a model category of reagents that meet some of these requirements. ODNs are synthetic polymers that are produced in highly purified quantities in a cost-effective way and the technology surrounding ODN synthesis has advanced dramatically in the last 10 years. Recently, Parekh-Olmedo et al. (*J. Mol. Neurosci.* 2004; 24(2):257-67) showed that certain classes of ODNs can inhibit aggregation. One of these groups is the G-rich ODN (GROs) class which have been used previously as aptamers to block protein function. Specifically, GROs have been shown to bind directly to STAT3 and interact with regions of the protein that enable dimerization and in another instance, GROs have been shown to block the integration of the HIV into the host chromosome by interacting with the HIV integrase. In both cases, the GRO forms a structure known as a G-quartet which arises from the association of four adjacent G-bases assembled into a cyclic conformation. These structures are stabilized by von Hoogstein hydrogen bonding and by base stacking interactions. These molecules exhibit a very compact structure which allows them to interact productively with functionally important protein domains.

Much of the focus on developing therapeutics that block aggregate formation comes from a wealth of data associating HD pathogenesis with the presence of cellular inclusion bodies. But, recent evidence from in vitro and in vivo studies suggest that Htt inclusions may not be toxic to the cell or lead to neuronal degeneration. In fact, Hayden and colleagues have created an exciting mouse model that shows no long term effect of Htt inclusions on behavior or viability. It may be true that inclusion bodies are neuroprotective and eliminating them may actually increase the potential for neurotoxicity.

Huntington's disease is caused by an increase in the length of the poly(Q) tract in the huntingtin (Htt) protein, which changes its solubility and induces aggregation. Aggregation occurs in two general phases, nucleation and elongation, and agents designed to block either phase are being considered as potential therapeutics.

Intracellular aggregates of Htt have long been considered phenotypic evidence of the neurodegenerative disorder Huntington's Disease. It is, however, not clear how the appearance of such inclusion bodies relates to the pathogenesis of the disease. A number of model systems have been designed to screen for therapeutic agents that can inhibit aggregation. Some of these assays measure the inhibition of fusion protein aggregation, proteins containing a fragment of Htt (here, GST-Q58-Htn) and a marker/reporter protein, often eGFP. The Htt component of this fusion protein harbors an expanded polyQ stretch.

As such, efforts to find a therapy for HD have focused on agents that disrupt or block the mutant Htt aggregation pathway.

It is well known in the art that G-rich DNA and RNA form inter- and intramolecular four-stranded structures known as G-quartets. G-quartets are formed when four G-bases are associated into a cyclic Hoogsten H-bonding arrangement wherein each G-base makes two H-bonds with its neighboring G-base. Ultimately, G-quartets stack on top of each other, giving rise to tetrad-helical structures. The stability of these G-quartets is related to several factors, including the presence of monovalent cations such as K+ and Na+, the concentration of G-rich ODNs present, and the sequence of the G-rich ODNs being used.

Many G-rich ODNs (GROs) have demonstrated significant cell-signaling factors. Identified GROs have been implicated in several cell functions and a variety of disorders. In particular, certain GROs display effective antiproliferative activity when added to cancer cell lines (Bates et al., Antiproliferative activity of G-rich ODNs correlates with protein binding, J. Biol. Chem., 274, 26369-26377 (1999); Xu et al., Inhibition of DNA replication and induction of S phase cell cycle arrest by G-rich ODNs, J. Biol. Chem., 276, 43221-43230 (2001); Dapic et al., Antiproliferative activity of G-quartet-forming ODNs with backbone and sugar modifications, Biochemistry, 41, 3676-3685 (2002)). Specifically, it has been reported that treatment of tumor cells with GROs inhibits cell cycle progression by interfering directly with DNA replication, as opposed to normal skin cells that exhibited minimal disruption of the cell cycle when treated with the same GROs (Xu et al.).

SUMMARY OF THE INVENTION

The present invention is based on the surprising and unexpected discovery that certain oligonucleotides are capable of disrupting protein aggregates that have been associated with disease pathologies. Therefore, the oligonucleotides of the invention can be used as therapeutics in the treatment and prevention of such diseases, and can also aid in the study of the diseases and their underlying physiological origins. In particular, the invention relates to guanosine-rich oligonucleotide compositions and associated methods of use to inhibit protein aggregates and their detrimental effects.

Although factors are known which lead to aggregation of proteins in the native state, for example, salting out, and isoelectric precipitation; the majority of cases of protein aggregation involve the intermolecular association of a partially-folded or "unfolded" intermediate state of the protein. The underlying reason is probably that partially-folded intermediates have hydrophobic patches, which normally pack together to yield the native state, but which can also interact in an intermolecular manner to form an aggregate. Diseases where protein aggregation is causal or an associated symptom and for which the present invention may be useful for treatment and/or prevention include Down's syndrome, Alzheimer's disease (AD), Parkinson's disease (PD), amyotrophic lateral sclerosis (ALS), and prion diseases such as bovine spongiform encephalitis (BSE) and Creutzfeldt-Jakob Disease (CJD), cystic fibrosis, and the so-celled polyglutamine diseases (TABLE 1), for example, Huntington's disease (HD), dentato-rubral and pallido-luysian atrophy (DRPLA) and several forms of spino-cerebellar ataxia (SCA), also have intracellular inclusions in regions corresponding to the regions of neuronal degeneration

TABLE 1

Summary of Polyglutamine Diseases.

| Disease | Gene name | Chromosomal location | Pattern of inheritance | Protein | Normal repeat length | Disease repeat length |
|---|---|---|---|---|---|---|
| Spinobulbar muscular atrophy (Kennedy disease) | AR | Xq13-21 | X-linked recessive | androgen receptor (AR) | 9-36 | 38-62 |
| Huntington disease | HD | 4p16.3 | autosomal dominant | huntingtin | 6-35 | 36-121 |
| Dentatorubral-pallidoluysian atrophy (Haw River syndrome) | DRPLA | 12p13.31 | autosomal dominant | atrophin-1 | 6-35 | 49-88 |
| Spinocerebellar ataxia type 1 | SCA1 | 6p23 | autosomal dominant | ataxin-1 | 6-44 | 39-82 |
| Spinocerebellar ataxia type 2 | SCA2 | 12q24.1 | autosomal dominant | ataxin-2 | 15-31 | 36-63 |
| Spinocerebellar ataxia type 3 (Machado-Joseph disease) | SCA3 | 14q32.1 | autosomal dominant | ataxin-3 | 12-40 | 55-84 |
| Spinocerebellar ataxia type 6 | SCA6 | 19p13 | autosomal dominant | $\alpha 1_A$-voltage-dependent calcium channel subunit | 4-18 | 21-33 |
| Spinocerebellar ataxia type 7 | SCA7 | 3p12-13 | autosomal dominant | ataxin-7 | 4-35 | 37-306 |
| Spinocerebellar ataxia type 17 | SCA17 | 6q27 | autosomal dominant | TATA binding protein | 25-42 | 45-63 |

In certain aspects the invention relates to isolated oligonucleotide compositions comprising from about 15 to about 50 nucleotides, and having at least 40% guanosine nucleotides. In certain embodiments the invention comprises oligonucleotides of SEQ ID NOs: 1-7. These gunosine rich oligonucleotides (GROs) have been shown to form higher order aggregates, for example, G-quartet structures, in which the GROs align in a parallel or antiparallel configuration. (See Biyani and Nisigaki, *Gene* 364: 130-38 (2005), incorporated herein by reference in its entirety). While not being limited to any particular theory, the inventors hypothesize that the higher-order structures of the GROs of the invention mediate their efficacy; i.e., inhibiting the aggregation of proteins, for example, the disease associated polyglutamine proteins. However, the GROs of the present invention may also be used generally to inhibit aggregation of other disease related proteins as indicated above. Therefore, in another aspect the oligonucleotide of the invention comprises a G-quartet structure. In a preferred embodiment, the isolated oligonucleotide of the invention comprises from 18-24 nucleotides, and has at least 95% guanosine nucleotides.

In other aspects the isolated GRO of the invention is disposed in a vector or plasmid nucleic acid for its convenient cloning, amplification, and/or transcription. In still other aspects the isolated GRO of the invention is operably linked to one or more transcription regulatory nucleic acid sequences. In yet another aspect, the isolated GRO is disposed in a vector or plasmid nucleic acid, and is operably linked with one or more transcription regulatory nucleic acid sequences.

In other aspects, the invention relates to a host cell comprising the isolated GRO of the invention. In certain embodiments, the host cell further comprises a vector or plasmid nucleic acid containing one or more transcription regulatory nucleic acid sequences operably linked with the GRO sequence of the invention. The vector or plasmid nucleic acids can be, for example, suitable for eukaryotic or prokaryotic cloning, amplification, or transcription. The vector or plasmid nucleic acids can also be stably integrated into the host cell's genome or maintained episomally.

In another aspect, the invention relates to method for inhibiting and/or reducing the aggregation of proteins. In other aspects, the invention relates to methods for inhibiting or reducing the aggregation of polyglutamine proteins, such as those that cause Huntington's Disease, or Spinocerebellar ataxia. In any embodiment of these aspects the invention comprises contacting an protein capable of forming a protein aggregate or a protein aggregate with an effective amount of a GRO of the invention to result in the inhibition of protein aggregate formation, the reduction of protein aggregation, and/or the dissociation of the components from a protein aggregate.

In other aspects, the invention relates to methods for treating and/or preventing a disease or condition in an individual related to the detrimental effects of protein aggregation. In certain embodiments, the methods of the invention comprise administering an effective amount of an isolated GRO in a pharmaceutically acceptable form to an individual in need thereof. In certain embodiments, the isolated GRO of the invention is administered together with a pharmaceutically acceptable carrier, excipient, adjuvant, amino acid, peptide, polypeptide, chemical compound, drug, biologically active agent or a combination thereof. As such, in another aspect the invention relates to therapeutic compositions comprising the isolated GRO of the invention in a pharmaceutically acceptable form together with at least one pharmaceutically acceptable carrier, excipient, adjuvant, amino acid, peptide, polypeptide, chemical compound, drug, biologically active agent or a combination thereof.

In certain embodiments the therapeutic GRO of the invention is complexed, bound, or conjugated to one or more chemical moieties to improve and/or modify, for example, bioavailability, half-life, efficacy, and/or targeting. In certain aspects of this embodiment, the GRO may be complexed or bound, either covalently or non-covalently with, for example, cationic molecules, salts or ions, lipids, glycerides, carbohydrates, amino acids, peptides, proteins, other chemical compounds, for example, phenolic compounds, and combinations thereof. In certain aspects the invention relates to a GRO of the invention conjugated to a polypeptide, for example, an antibody. In certain embodiments the antibody is specific for the protein or protein aggregate of interest and therefore targets the GRO to the protein and/or protein aggregate.

The therapeutic GRO of the invention can be administered by any suitable route recognized by those of skill in the art, for example, enteral, intravenous, intra-arterial, parenteral, topical, transdermal, nasal, and the like. In addition, the therapeutic may be in any pharmaceutically acceptable form such as, for example, a liquid, lyophilized powder, gel, pill, controlled release capsule, and the like, which is now known or becomes known to those of skill in the art.

Additional advantageous features and functionalities associated with the compositions, methods, and processes of the present invention will be apparent from the drawings presented herein, as well as the detailed description which follows. The publications and other materials used herein to illuminate the background of the invention, and in particular cases, to provide additional details respecting the practice, are incorporated by reference, and for convenience are listed in the appended bibliography.

DETAILED DESCRIPTION OF THE INVENTION

Figure 1:
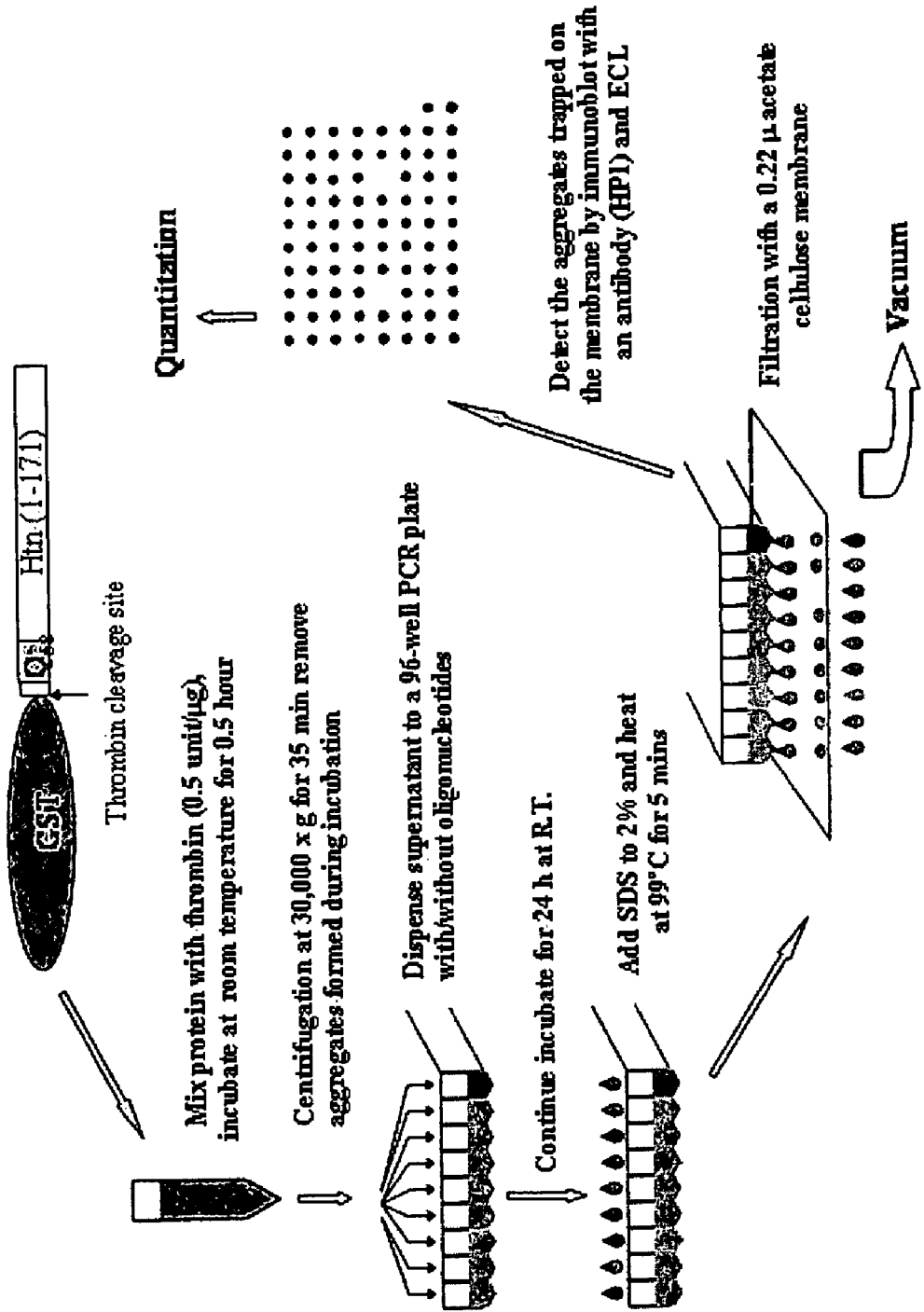
FIG. 1 is a diagram of the biochemical model screening assay obtained from Wang et al. (2005) and illustrating the steps involved in the biochemical/immunoblotting assay. The fusion protein GST-Q58-Htn (20 μg/ml) was mixed with thrombin (0.5 unit/μg protein) for 30 minutes and the mixture centrifuged to remove aggregated protein. The soluble protein was mixed with an ODN in a 96-well PCR plate and incubated for 24 hours at room temperature (RT). SDS was added to a final concentration of 2% and the mixture heated at 99° C. for 5 minutes. Filtration through a 0.22 micron acetate cellulose membrane filter was followed by detection of aggregated Q58-Htn fragment by immunoblotting with an antibody (HP1) and ECL. Quantitation was carried out using an ImageQuant program. The blot displays both positive and negative results—positions lacking a black spot indicate that aggregation was inhibited by the ODN.

The present invention is based on the surprising an unexpected discovery that certain oligonucleotides are capable of inhibiting protein aggregation. The invention includes oligonucleotide compositions useful for research and therapeutic purposes.

The term "oligonucleotide" refers generally to, and interchangeably with nucleic acids, deoxyribonucleotides, deoxyribonucleic acids, ribonucleotides, and ribonucleic acids, and polymeric forms thereof, and includes either single- or double-stranded forms. Also, unless expressly limited, the term "nucleotide" includes known analogues of natural nucleotides that have similar binding properties as the reference nucleic acid, for example, peptide nucleic acids (PNAs). In addition, a particular nucleotide or nucleic acid sequence includes complementary sequences, and the sequence explicitly indicated. The term nucleic acid is generic to the terms "gene," "DNA," "cDNA," "oligonucleotide," "RNA," "mRNA," "nucleotide," "polynucleotide," and the like. The four nucleotide bases are guanine, cytosine, thymine, uracil and adenine. Nucleotides are composed of a pentose sugar, a purine or pyrimidine base, and a phosphate group (i.e., adenosine, guanosine, cytidine, uridine, and thymidine).

As used herein, the term "oligonucleotide" refers to a series of linked nucleotide residues. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise a nucleic acid sequence having about 10 nt, 50 nt, or 100 nt in length, preferably about 15 nt to 30 nt in length. In certain embodiments of the invention, an oligonucleotide comprising a nucleic acid molecule less than 100 nt in length would further comprise at least 6 contiguous nucleotides of SEQ ID NOS: 1-12.

As used herein, the terms "GRO", "aptameric GRO", and "G-rich oligonucleotides" are used interchangeably. Aptameric oligonucleotide molecules bind a specific target molecule such as small molecules, proteins, nucleic acids, and even cells, tissues and organisms. Aptamers offer the utility for biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

Oligonucleotides may be chemically synthesized and may also be used as probes. Nucleic acid synthesizers are available to synthesize oligonucleotides of any desired sequence. Certain oligonucleotide analogs may also be readily synthesized by modifying the reactants and reaction conditions. For example, phosphorothioate and methylphosphonate oligonucleotides may be synthesized using commercially available automated oligonucleotide synthesizers.

An oligonucleotide's binding affinity to a complementary nucleic acid may be assessed by determining the melting temperature ($T_M$) of a hybridization complex. The $T_M$ is a measure of the temperature required to separate the nucleic acid strands of a hybridization complex. The $T_M$ may be measured by using the hybridization complex's UV spectrum to assess the degree and strength of hybridization. During hybridization, base stacking occurs which reduces the UV absorption of the nucleic acid. By monitoring UV absorption and the resulting increase in UV absorption that occurs during strand separation, one may assess the hybridization affinity of a nucleic acid for its complement.

The structure and stability of hybridization complexes may be further assessed using NMR techniques known to those skilled in the art.

A vast array of oligonucleotide analogs exist that achieve the same functionality as naturally occurring oligonucleotides. There is extensive literature setting forth an almost limitless variety of modifications that can be used to generate oligonucleotide analogs. The phosphate, sugar, and/or base moieties may be modified and/or replaced by the introduction/removal of chemical groups and/or bonds. Many oligonucleotide analogs have superior properties to those of naturally occurring oligonucleotides. Such superior properties include, but are not limited to, increased hybridization affinity and/or resistance to degradation.

"Nucleic acid template," or "parental nucleic acid" refers to a nucleic acid that has served as a template for a subsequent step or process. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

The term "gene" is used broadly to refer to any segment of nucleic acid associated with expression of a given RNA or protein. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have specifically desired parameters.

A "recombinant" nucleic acid is any nucleic acid produced by an in vitro or artificial (meaning not naturally occurring) process or by recombination of two or more nucleic acids. The recombinant nucleic acids and referred to herein are not intended to limit the scope of the present invention, which one of ordinary skill will recognize, contemplates the use of any guanosine-rich oligonucleotide. Nucleic acid modifications include those obtained by site-specific mutation, shuffling, endonuclease digestion, PCR, subcloning, methylation, acetylation, chemical modification, and related techniques.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS IN MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990) C&EN 36-47; Sakamoto, et al., Laboratory evolution of toluene dioxygenase to accept 4-picoline as a substrate. *Appl. Environ. Microbiol.* 67:3882-3887 (2001); Lueng, et al., A method for random mutagenesis of a defined DNA segment using a modified polymerase chain reaction. *Technique: J Methods Cell Molec Biol* 1(1):11-15 (1989).

The term "host cell" includes a cell that might be used to carry an exogenous nucleic acid, a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or cells that contain a nucleic acid endogenous to the cell that has been artificially modified without removing the nucleic acid from the cell.

The terms "degree of similarity" or "identity," in the context of two or more nucleic acid sequences, refer to two or more sequences or subsequences that are the same or homologous and have a specified percentage of nucleotides that are the same, when compared and aligned for maximum correspondence, as measured using one of the sequence comparison algorithms such as BLAST, ClustalW, or other algorithms available to persons of skill or by visual inspection. For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Other determinations of homology include hybridization of nucleic acids under stringent conditions. The phrase "hybridizing," refers to the binding, duplexing, or hybridizing of a molecule only to a particular nucleotide sequence under stringent conditions, including when that sequence is present in a complex mixture (e.g., total cellular) DNA or RNA.

A nucleic acid "operon" includes a gene that is situated in a functional relationship, i.e., operably linked, with other nucleic acid sequences, for example, a promoter, an enhancer, termination signals, or another gene if it increases the transcription of the coding sequence.

As used herein, "GRO" refers generally to guanosine (or guanine)-rich oligonucleotides.

As used herein, "HDG" refers to an oligonucleotide comprised completely of guanosine (G) nucleotides. (See SEQ ID NO:3).

As used herein, "HDA" refers to an oligonucleotide comprised completely of adenosine (A) nucleotides. (See SEQ ID NO:9).

As used herein, "HDC" refers to an oligonucleotide comprised completely of cytidine (C) nucleotides. (See SEQ ID NO:8).

As used herein, "HDT" refers to an oligonucleotide comprised completely of thymidine (T) nucleotides (See SEQ ID NO:10).

As used herein, "ODN" refers generally to a synthetic oligonucleotide of length n, comprising any combination of nucleotides.

"Derivatives" are modified nucleic acid sequences formed from the native compounds either directly, by modification, or by partial substitution. "Analogs" are nucleic acid sequences or amino acid sequences that have a structure similar to, but not identical to, the native compound, e.g. they differ from it in respect to certain components or side chains. Analogs may be synthetic or derived from a different evolutionary origin and may have a similar or opposite metabolic activity compared to wild type.

Derivatives and analogs may be full length or other than full length. Derivatives or analogs of the nucleic acids or proteins of the invention include, but are not limited to, molecules comprising regions that are substantially homologous to the nucleic acids or proteins of the invention, in various embodiments, by at least about 30%, 45%, 70%, 80%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Nucleic acid derivatives and modifications include those obtained by gene replacement, site-specific mutation, deletion, insertion, recombination, repair, shuffling, endonuclease digestion, PCR, subcloning, and related techniques.

In certain embodiments, the invention comprises an isolated polynucleotide sequence, for example, the isolated aptameric GROs of SEQ ID NOs: 1-12. By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an automatically replicating plasmid or virus; or into the genomic DNA of a prokaryote or eukaryote, or which exists as a separate molecule (e.g., a cDNA) independent of other sequences. The nucleotides can be modified forms of DNA or RNA.

The present invention relates to the finding that guanosine (G) rich oligonucleotides (GROs) form functional aptamers, and are effective inhibitors of protein aggregation, for example, the aggregation of polyglutamine proteins such as huntingtin protein, which is associated with Huntington's Disease (HD). As such, the isolated GROs of the invention have therapeutic potential and can be used as a treatment for patients with diseases and conditions resulting from detrimental effects of protein aggregation, for example, Huntington's disease. While not being limited by any particular theory, the inventors postulate that the beneficial effect observed with the GROs of the invention may result from the inhibition or slowing of the aggregation process. The GROs of the invention that possess aptameric activity may also be beneficial in other amyloid or neurodegenerative diseases, for example, Alzheimer's Disease, Parkinson's Disease, spinocerebellar ataxia, and prion diseases. Moreover, the GROs of the present invention can be used to examine the relationship between cellular aggregates and toxicity in various model systems.

Therefore, in one embodiment the polynucleotide composition of the invention comprises an isolated aptameric oligonucleotide having from about 15 to about 50 nucleotides, and having at least 40% guanosine nucleotides. In certain embodiments the invention comprises oligonucleotides of SEQ ID NOs: 1-12. In another embodiment, the oligonucleotides of the invention are capable of forming G-quartet structures.

G-rich DNA and RNA have the ability to form inter- and intramolecular four-stranded structures, referred to as G-quartets. (See Biyani and Nisigaki, Gene 364: 130-38 (2005)). G-quartets arise from the association of four G-bases into a cyclic Hoogsteen H-bonding parallel or anti-parallel arrangement, and each G-base makes two hydrogen bonds with its neighbor G-base (N1 to O6 and N2 to N7). G-quartets stack on top of each other to give rise to tetrad-helical structures. The stability of G-quartet structures depends on several factors: the presence of the monovalent cations, the concentration of the G-rich oligonucleotides present, and the sequence of the G-rich oligonucleotides under study. Potassium with the optimal size to interact within a G-octamer greatly promotes the formation of G-quartet structures and increases their stability. G-quartet oligodeoxynucleotides (GQ-ODNs) have been suggested to play a critical role in several biological processes including modulation of telomere activity, inhibition of human thrombin, HIV infection, HIV-1 integrase activity, human nuclear topoisomerase 1 activity, and DNA replication in vitro. On the basis of the structure and mechanism of Stat3 activation, G-quartet-forming oligonucleotides were developed recently to block Stat3 activity within cancer cells.

While there is no hard rule governing what specific nucleotide sequence will result in the G-quartet structure, they can usually form with some iteration of a guanosine repeat, for example, $GGTT_n$. Thus, as along as the guanosines can come in contact via parallel or anti paralell positioning, then the oligonucleotides can form higher-order structures such as the G-quartet structure. As such, the sequence of the aptameric oligonucleotide of the invention can be varied in any number of ways as long as the oligonucleotide comprises from about 15 to about 50 nucleotides, comprises at least 40% guanosine nucleotides. In a preferred embodiment, the aptameric oligonucleotides form a G-quartet structure. In certain embodiments, the invention comprises an aptameric oligonucleotide of SEQ ID NOs:1-12.

While not being limited to any particular theory, the inventors hypothesize that the higher-order structures of the aptameric GROs of the invention mediate their efficacy; i.e., inhibiting the aggregation of proteins, for example, the disease associated polyglutamine proteins. However, the aptameric GROs of the present invention may also be used generally to inhibit aggregation of other disease related proteins as indicated above. In a preferred embodiment, the isolated aptameric oligonucleotide of the invention comprises from 18-24 nucleotides, and has at least 95% guanosine nucleotides. In a particularly preferred embodiment, the invention comprises the GRO of SEQ ID NO:3. By utilizing a biochemical assay as an initial screen, SEQ ID NO:3 inhibited Htt aggregation. The monotonic G-ODN of the invention was also able to improve cell survival in PC12 cells overexpressing a mutant Htt fragment fusion gene.

In any of the embodiments described herein, the aptameric GRO of the invention may comprise one or more modified nucleotides or nucleotide analogs. Nucleotide modifications can be incorporated during or after oligonucleotide synthesis, and include modifications of the nucleobase, the sugar moiety, and/or the phosphate group.

Phosphodiester Moiety Analogs. Numerous analogs to the naturally occurring phosphodiester backbone have been used in oligonucleotide design. Phosphorothioate, phosphorodithioate, and methylphosphonate are readily synthesized using known chemical methods. Because novel nucleotide linkages can be synthesized manually to form a dimer and the dimer later introduced into the oligonucleotide via automated synthesis, the range of potential backbone modifications is as broad as the scope of synthetic chemistry. For example, the oligonucleotide may be substituted or modified in its internucleotide phosphate residue with a thioether, carbamate, carbonate, acetamidate or carboxymethyl ester.

Unlike the naturally occurring phosphodiester moieties, many phosphodiester analogs have chiral centers. For example, phosphorothioates, methylphosphonates, phosphoramidates, and alkyl phosphotriesters all have chiral centers. One skilled in the art would recognize numerous other phosphodiester analogs that possess chiral centers. Because of the importance of stereochemistry in hybridization, the stereochemistry of phosphodiester analogs can influence the affinity of the oligonucleotide for its target.

Most phosphodiester backbone analogs exhibit increased resistance to nuclease degradation. In an embodiment, phosphorothioates, methyl phosphonates, phosphorimidates, and/or phosphotriesters are used to achieve enhanced nuclease resistance. Increased resistance to degradation may also be achieved by capping the 5' and/or 3' end of the oligonucleotide. In an embodiment, the 5' and/or 3' end capping of the oligonucleotide is via a 5'-5' and/or 3'-3' terminal inverted linkage.

Phosphorothioate oligodeoxynucleotides are relatively nuclease resistant, water soluble analogs of phosphodiester oligodeoxynucleotides. These molecules are racemic, but still hybridize well to their RNA targets. Stein, C., et al. (1991) Pharmac. Ther. 52:365 384. Phosphorothioate oligonucleotides may be stereo regular, stereo non-regular or stereo random. A stereo regular phosphorothioate oligonucleotide is a phosphorothioate oligonucleotide in which all of the phosphodiester linkages or phosphorothiodiester linkages polarize light in the same direction. Each phosphorous in each linkage may be either an $S_p$ or $R_p$ diastereomer.

Sugar Moiety Analogs. Oligonucleotide analogs may be created by modifying and/or replacing a sugar moiety. The sugar moiety of the oligonucleotide may be modified by the addition of one or more substituents. For example, one or more of the sugar moieties may contain one or more of the following substituents: amino-alkylamino, araalkyl, heteroalkyl, heterocycloalkyl, aminoalkylamino, O, H, an alkyl, polyalkylamino, substituted silyl, F, Cl, Br, CN, $CF_3$, $OCF_3$, OCN, O-alkyl, S-alkyl, SOMe, $SO_2Me$, $ONO_2$, NH-alkyl, $OCH_2CH$=$CH_2$, $OCH_2CCH$, OCCHO, allyl, O-allyl, $NO_2$, $N_3$, and $NH_2$.

Modification of the 2' position of the ribose sugar has been shown in many instances to increase the oligonucleotide's resistance to degradation. For example, the 2' position of the sugar may be modified to contain one of the following groups: H, OH, OCN, O-alkyl, F, CN, $CF_3$, allyl, O-allyl, $OCF_3$, S-alkyl, SOMe, $SO_2Me$, $ONO_2$, $NO_2$, $N_3$, $NH_2$, NH-alkyl, or $OCH$=$CH_2$, OCCH, wherein the alkyl may be straight, branched, saturated, or unsaturated.

In addition, the oligonucleotide may have one or more of its sugars modified and/or replaced so as to be a ribose or hexose (i.e. glucose, galactose). Further, the oligonucleotide may have one or more modified sugars. The sugar may be modified to contain one or more linkers for attachment to other chemicals such as fluorescent labels. In an embodiment, the sugar is linked to one or more aminoalkyloxy linkers. In another embodiment, the sugar contains one or more alkylamino linkers. Aminoalkyloxy and alkylamino linkers may be attached to biotin, cholic acid, fluorescein, or other chemical moieties through their amino group.

Base Moiety Analogs. In addition, the oligonucleotide may have one or more of its nucleotide bases substituted or modified. In addition to adenine, guanine, cytosine, thymine, and uracil, other bases such as inosine, deoxyinosine, hypoxanthine may be used. In addition, isoteric purine 2'deoxy-furanoside analogs, 2'-deoxynebularine or 2'deoxyxanthosine, or other purine or pyrimidine analogs may also be used. By carefully selecting the bases and base analogs, one may fine tune the binding properties of the oligonucleotide. For example, inosine nay be used to reduce hybridization specificity, while diaminopurines may be used to increase hybridization specificity.

Adenine and guanine may be modified at positions N3, N7, N9, C2, C4, C5, C6, or C8 and still maintain their hydrogen bonding abilities. Cytosine, thymine and uracil may be modified at positions N1, C2, C4, C5, or C6 and still maintain their hydrogen bonding abilities.

Some base analogs have different hydrogen bonding attributes than the naturally occurring bases. For example, 2-amino-2'-dA forms three, instead of the usual two, hydrogen bonds to thymine (T). Examples of base analogs that have been shown to increase duplex stability include, but are not limited to, 5-fluoro-2'-dU, 5-bromo-2'-dU, 5-methyl-2'-dc, 5-propynyl-2'-dC, 5-propynyl-2'-dU, 2-amino-2'-dA, 7-deazaguanosine, 7-deazadenosine, and N2-Imidazoylpropyl-2'-dG.

Pendant Groups. A "pendant group" may be linked to the oligonucleotide. Pendant groups serve a variety of purposes which include, but are not limited to, increasing cellular uptake of the oligonucleotide, enhancing degradation of the target nucleic acid, and increasing hybridization affinity. Pendant groups can be linked to any portion of the oligonucleotide but are commonly linked to the end(s) of the oligonucleotide chain. Examples of pendant groups include, but are not limited to: acridine derivatives (i.e. 2-methoxy-6-chloro-9-aminoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe(II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; phenolic groups, radioactive markers; nonradioactive markers such as dyes; and polylysine or other polyamines.

In one embodiment, the aptameric oligonucleotide of the invention contains at least one nucleotide conjugated to a carbohydrate, sulfated carbohydrate, or gylcan. Conjugates may be regarded as a way as to introduce a specificity into otherwise unspecific DNA binding molecules by covalently linking them to a selective oligonucleotide or polypeptide.

Cellular Uptake. To enhance cellular uptake, the oligonucleotide may be administered in combination with a carrier or lipid. For example, the oligonucleotide may be administered in combination with a cationic lipid. Examples of cationic lipids include, but are not limited to, lipofectin, dotma, dope, DMRIE and DPPES. The oligonucleotide may also be administered in combination with a cationic amine such as poly (L-lysine). Oligonucleotide uptake may also be increased by conjugating the oligonucleotide to chemical moieties such as transferrin and cholesteryls. In addition, oligonucleotides may be targeted to certain organelles by linking specific chemical groups to the oligonucleotide. For example, linking the oligonucleotide to a suitable array of mannose residues will target the oligonucleotide to the liver.

The cellular uptake and localization of oligonucleotides may be monitored by using labeled oligonucleotides. Methods of labeling include, but are not limited to, radioactive and fluorescent labeling. Fluorescently labeled oligonucleotides may be monitored using fluorescence microscopy and flow cytometry.

The efficient cellular uptake of oligonucleotides is well established. For example, when a 20 base sequence phosphorothioate (PS) oligonucleotide was Injected into the abdomens of mice, either intraperitoneally (IP) or intravenously (IV). The oligonucleotide accumulated in the kidney liver, and brain. Chain-extended oligonucleotides were also observed. Argrawal, S., et al. (1988) Proc. Natl. Acad. Sci. U.S.A. 85:7079 7083. When the PS 27-oligonucleotide was given by IV to rats, the initial $T_{1/2}$ (transit out of the plasma) was 23 min, while the $T_{1/2}$beta of total body clearance was 33.9 hours. The long beta half-life of elimination demonstrates that dosing could be infrequent and still maintain effective, therapeutic tissue concentrations. Iverson, P. (1991) Anti-Cancer Drug Des. 6:531.

Another aspect of the invention pertains to vectors, containing an aptameric GRO of the invention, for example, nucleic acid encoding SEQ ID NOs: 1-12, or derivatives thereof for its convenient cloning, amplification, and/or transcription. As used herein, the term "vector" refers to a nucleic acid molecule capable of transporting another nucleic acid to which it has been "operably linked." One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the transcription of sequences to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), and artificial chromosomes, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be transcribed. Within a recombinant expression vector, "operably-linked" is intended to mean that the nucleotide sequence of interest is linked to the regulatory sequence(s) in a manner that allows for transcription and/or expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of transcription, and/or expression of protein desired, etc. The expression vectors of the invention can be introduced into host cells to thereby produce proteins or peptides, including fusion proteins or peptides, encoded by nucleic acids as described herein. The recombinant expression vectors of the invention can be designed for transcription and/or expression in prokaryotic or eukaryotic cells. For example, transcription and/or expression in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and/or translated in vitro, for example using T7 promoter regulatory sequences and T7 polymerase.

In another embodiment, the recombinant vector is capable of directing transcription of the aptameric GRO preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banedji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264, 166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

In other aspects, the invention relates to a host cell comprising the isolated aptameric GRO of the invention. In certain embodiments, the host cell comprises a vector, plasmid or artificial chromosome nucleic acid containing one or more transcription regulatory nucleic acid sequences operably linked with the aptameric GRO sequence of the invention. The vector or plasmid nucleic acids can be, for example, suitable for eukaryotic or prokaryotic cloning, amplification, or transcription. In other embodiments, the invention comprises a plurality of aptameric GRO sequences linked contiguously as a single polynucleotide chain. In still other embodiments, the invention comprises a nucleic acid vector containing a plurality of aptameric GRO sequences linked contiguously and operably linked with the nucleic acid sequence of the vector.

The term "host cell" includes a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. For example, bacteria cells may be used to carry or clone nucleic acid sequences or express polypeptides. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce the aptameric GRO of the invention.

In another aspect, the invention relates to method for inhibiting and/or reducing the aggregation of proteins. In other aspects, the invention relates to methods for inhibiting or reducing the aggregation of polyglutamine proteins, such as those that cause Huntington's Disease, or Spinocerebellar ataxia. In any embodiment of these aspects the invention comprises contacting an protein capable of forming a protein aggregate or a protein aggregate with an effective amount of a GRO of the invention to result in the inhibition of protein aggregate formation, the reduction of protein aggregation, and/or the dissociation of the components from a protein aggregate.

Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system. Suitable hosts include microbes such as bacteria, yeast, insect or mammalian organisms or cell lines. Examples of suitable bacteria are *E. coli* and *B. subtilis*. A preferred yeast vector is pRS426-Gal. Examples of suitable yeast are *Saccharomyces* and *Pichia*. Suitable amphibian cells are *Xenopus* cells. Suitable vectors for insect cell lines include baculovirus vectors. Mouse, rat or human cells are preferred mammalian cells.

Transformation of a host cell with recombinant DNA may be carried out by conventional techniques as are well known to those skilled in the art. By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., an INDY polypeptide), or fragment thereof.

Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. Another method is to use a eukaryotic viral vector, such as simian virus 40 (SV40) or bovine papilloma virus, to transiently infect or transform eukaryotic cells. (Eukaryotic Viral Vectors, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*) or may be a mammalian cell, including a human cell.

Mammalian cell systems that utilize recombinant viruses or viral elements to direct expression may be engineered. For example, when using adenovirus expression vectors, the nucleic acid sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the polypeptides in infected hosts (e.g., Logan & Shenk, Proc. Natl. Acad. Sci. U.S.A. 81:3655-3659, 1984).

For long-term, high-yield production of recombinant genes, stable expression is preferred. Rather than using expression vectors that contain viral origins of replication, host cells can be transformed with the cDNA encoding an aptameric GRO controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci, which in turn can be cloned and expanded into cell lines. For example, following the introduction of foreign DNA, engineered cells may be allowed to grow for 1 to 2 days in an enriched media, and then are switched to a selective media. A number of selection systems may be used, including but not limited to the herpes simplex virus thymidine kinase (Wigler et al., Cell 11: 233, 1977), hypoxanthine-guanine phosphoribosyltransferase (Szybalska & Szybalski, Proc. Natl. Sci. U.S.A. 48: 2026, 1962), and adenine phosphoribosyltransferase (Lowy et al., Cell 22: 817, 1980) genes can be employed.

In other aspects, the invention relates to methods for treating and/or preventing a disease or condition in an individual related to the detrimental effects of protein aggregation. In certain embodiments, the methods of the invention comprise administering an effective amount of an isolated GRO in a pharmaceutically acceptable form to an individual in need thereof. In certain embodiments, the isolated GRO of the invention is administered together with a pharmaceutically acceptable carrier, excipient, adjuvant, amino acid, peptide, polypeptide, chemical compound, drug, biologically active agent or a combination thereof. As such, in another aspect the invention relates to therapeutic compositions comprising the isolated GRO of the invention in a pharmaceutically acceptable form together with at least one pharmaceutically acceptable carrier, excipient, adjuvant, amino acid, peptide, polypeptide, chemical compound, drug, biologically active agent or a combination thereof.

In certain embodiments the therapeutic GRO of the invention is complexed, bound, or conjugated to one or more chemical moieties to improve and/or modify, for example, bioavailability, half-life, efficacy, and/or targeting. In certain aspects of this embodiment, the GRO may be complexed or bound, either covalently or non-covalently with, for example, cationic molecules, salts or ions, lipids, glycerides, carbohydrates, amino acids, peptides, proteins, other chemical compounds, for example, phenolic compounds, and combinations thereof. In certain aspects the invention relates to a GRO of the invention conjugated to a polypeptide, for example, an antibody. In certain embodiments the antibody is specific for the protein or protein aggregate of interest and therefore targets the GRO to the protein and/or protein aggregate.

The efficacy of oligonucleotide therapy is also well established. For example, when a 24-base sequence PS oligonucleotide targeted to human c-myb mRNA was infused, through a miniosmotic pump, into scid mice bearing the human K562 chronic myeloid leukemia cell line, mean survival times of the mice treated with the antisense oligonucleotides were six- to eightfold longer than those of mice untreated or treated with the sense controls or treated with an oligonucleotide complementary to the c-kit proto-oncogene mRNA. Ratajczak, et al. (1992) Proc. Natl. Acad. Sci. U.S.A. 89:11823.

Therapeutic uses and formulations. The nucleic acids and proteins of the invention are useful in potential prophylactic and therapeutic applications implicated in a variety of disorders including, but not limited to: metabolic disorders, diabetes, obesity, infectious disease, anorexia, cancer, neurodegenerative disorders, Huntington's Disease, Alzheimer's Disease, Parkinson's Disorder, prion diseases (e.g., BSE and CJD), spinocerebellar ataxia, immune disorders, hematopoietic disorders, and the various dyslipidemias, metabolic disturbances associated with obesity, the metabolic syndrome X and wasting disorders associated with chronic diseases and various cancers, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, lupus erythematosus, obesity, transplantation, adrenoleukodystrophy, congenital adrenal hyperplasia, prostate cancer, neoplasm; adenocarcinoma, lymphoma, uterus cancer, fertility, leukemia, hemophilia, hypercoagulation, idiopathic thrombocytopenic purpura, immunodeficiencies, graft versus host disease, AIDS, bronchial asthma, rheumatoid and osteoarthritis, Crohn's disease; multiple sclerosis, treatment of Albright Hereditary Ostoeodystrophy, and other diseases, disorders and conditions of the like.

Preparations for administration of the therapeutic complex of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The nucleic acid molecules, polypeptides, and antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the therapeutic complex of the invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

A therapeutically effective dose refers to that amount of the therapeutic complex sufficient to result in amelioration or delay of symptoms. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, intravenous, intraperitoneal, parenteral or rectal administration.

Also disclosed according to the present invention is a kit or system utilizing any one of the methods, selection strategies, materials, or components described herein. Exemplary kits according to the present disclosure will optionally, additionally include instructions for performing methods or assays, packaging materials, one or more containers which contain an assay, a device or system components, or the like.

In an additional aspect, the present invention provides kits embodying the complex and methods of using disclosed herein. Kits of the invention optionally include one or more of the following: (1) polypeptide or nucleic acid components described herein; (2) instructions for practicing the methods described herein, and/or for operating the selection procedure herein; (3) one or more detection assay components; (4) a container for holding nucleic acids or polypeptides, other nucleic acids, transgenic plants, animals, cells, or the like and, (5) packaging materials.

While preferred embodiments of the invention have been shown and described herein, it will be understood that such embodiments are provided by way of example only. Numerous variations, changes and substitutions will occur to those skilled in the art without departing from the spirit of the invention in view of the present description and examples. Accordingly, it is intended that the appended claims cover all such variations as fall within the spirit and scope of the invention.

EXAMPLES

The original observation that ODNs bearing random sequences reduced Htt aggregate formation prompted a closer examination of a potential role for ODNs in HD therapy. We chose to utilize a biochemical/immunochemical assay system that enables rapid screening of compounds/molecules for the inhibition of Htt aggregation. In this test, ODNs (40 μm) were mixed with purified mutant Huntington for 24 hours and then passed through a cellulose acetate membrane filter (0.2 μm). The percentage of aggregates remaining on the filter was detected by immunochemistry using a primary HD-antibody and a secondary anti-rabbit antibody conjugated to alkaline phosphatase. Included in these experiments was a positive control, Congo Red. Two ODNs, HD3S/53 (all DNA, 53-mer) and HDR/25NS (all RNA, 25-mer), were found to be effective inhibitors. Fundamentally, the results established that ODNs can be used to inhibit Huntington aggregation. These molecules however ranged in size up to 53 bases and some were found to be unstable in cells, showing little inhibitory activity. This work was published and the paper is incorporated by reference herein in its entirety (Parekh-Olmedo, et al., Modified Single-Stranded ODNs inhibit Aggregate Formation and Toxicity Induced by Expanded Polyglutamine, *Journal of molecular Science*, Vol. 24, pp. 257-267, (2004)). Having established that ODNs have potential as a possible HD therapeutic, we turned our attention toward screening ODNs with specific, yet simple, sequences. As a starting point, we designed 20-mers of monomeric sequences (all Gs, Ts, Cs or As) and passed them through the biochemical assay described above. The three ODNs, referred to herein as Huntington's Disease (HD) A, G, T, or C oligonucleotides: HDA (SEQ ID NO:9), HDG (SEQ ID NO:3), HDT (SEQ ID NO:10) and HDC (SEQ ID NO:8), respectively.

Figure 4:
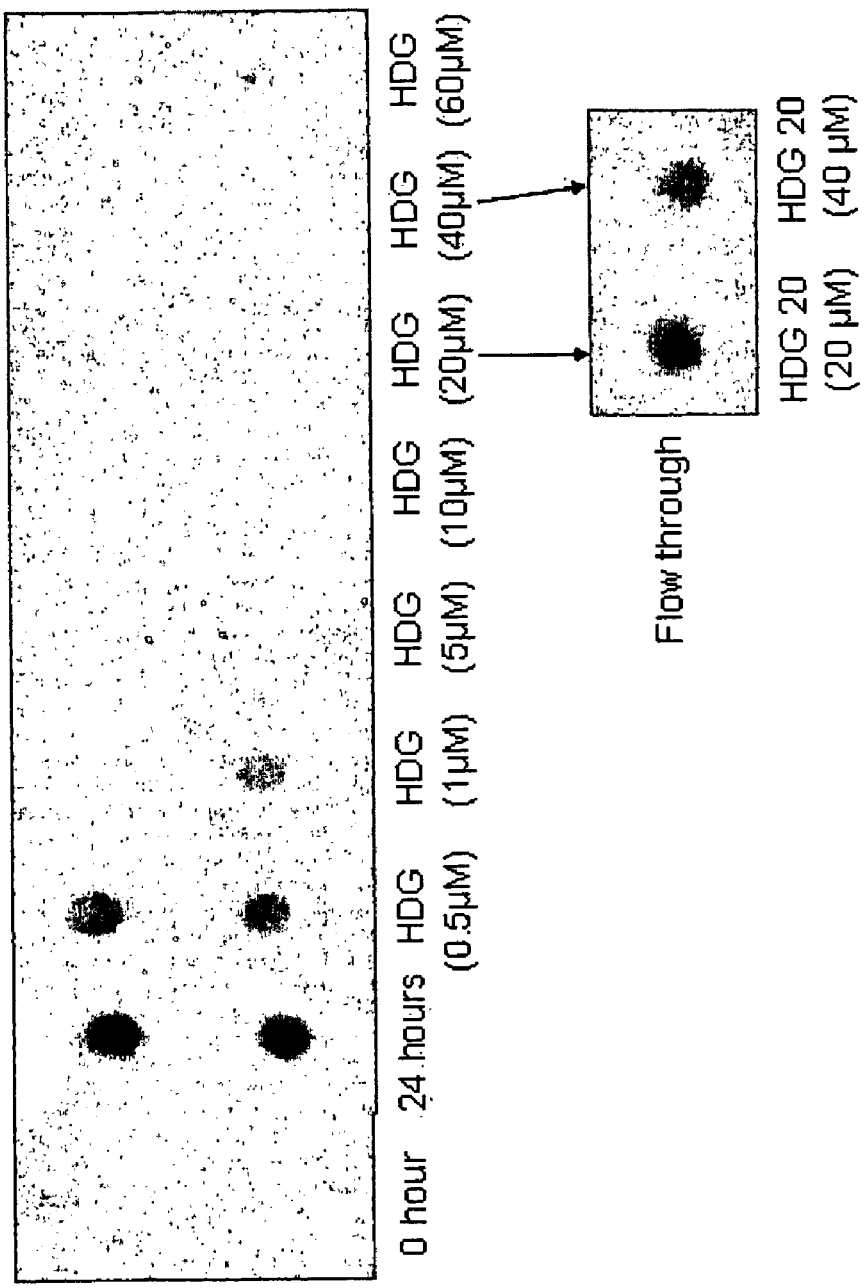
FIG. 4 is a dot blot analysis of HDG 20 (SEQ ID NO:3) activity on aggregation of mutant Htt fragment. HDG 20, a 20-base monotonic guanosine ODN, was tested in the assay outlined in FIG. 1 (see legend) at the indicated concentration. The reaction was carried out 4 times in duplicate for 24 hours and a representative blot from the four independent experiments is shown. 0 hour, reaction mixture stopped at time zero; 24 hours, control reaction lacking ODNs. (Inset), The Flow-through from filter binding reaction containing HDG 20 (20 µM or 40 µM) was placed on blotting paper, dried and processed as described in the legend to FIG. 1.
Figure 6:
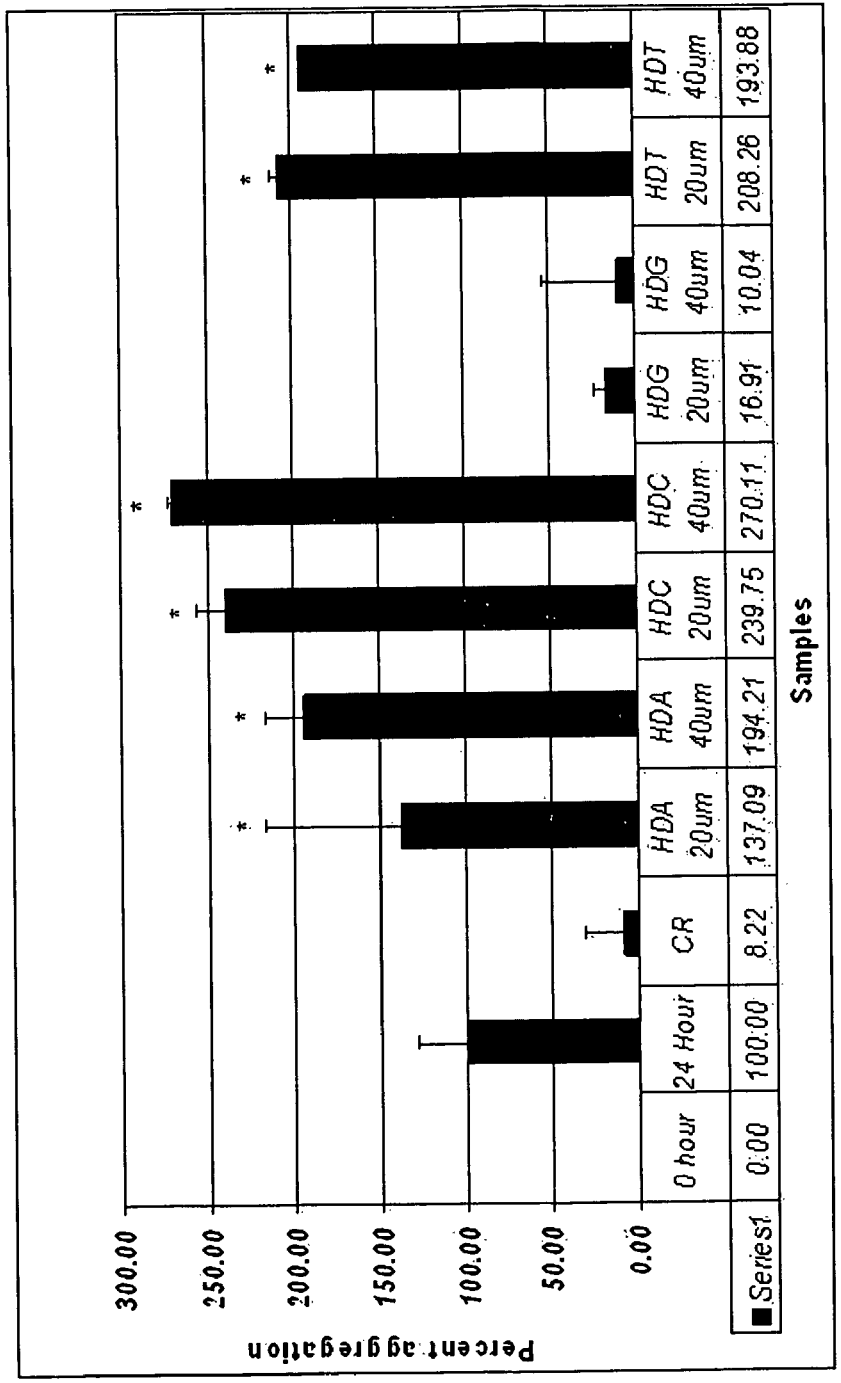
FIG. 6 is a bar graph depicting blots carried out to test monotonic 20-mers. Average aggregation levels, representative of 5 independent experiments with standard deviation and average values (Series 1) presented. *, denotes significance $p<0.05$ as compared to Congo Red (control) as determined by a one way ANOVA with Tukey's post hoc test.

As shown in FIG. 6, HDA, HDC and HDT (SEQ ID NOs: 8, 9, and 10) are unable to inhibit aggregate formation in the biochemical assay at either 20 μM or 40 μM. In sharp contrast, HDG (SEQ ID NO:3) was remarkably efficient in blocking aggregation rivaling Congo Red in activity. In some cases, no aggregates were retained on the filter falling below our capacity to detect them. This result was repeated numerous times (>10) and was judged to be robust and reproducible. Thus, we pursued the HDG molecule as a possible therapeutic for HD by examining its activity at various doses in the biochemical assay. As seen in FIG. 4, low levels of HDG exhibited high levels of inhibition activity, confirming our earlier results. This dose curve was extremely reproducible with 1-5 μM concentrations producing a near complete inhibition of Htt aggregation. We were unable to detect any Htt aggregate inhibition catalyzed by HDA, HDT and HDC at similar levels.

When the concentrations exceeded 60 μM; we observed small but nonreproducible positive and negative effects (data not shown). Thus, we ended this line of experimentation and focused once again on the basic G-rich ODN, HDG (SEQ ID NO:3).

Agents demonstrating positive effects in any biochemical assay must be capable of inhibiting Htt aggregation in cells. One of the most versatile and robust test systems utilizes the human embryonic kidney cell line, HEK293T cells.

A well-established biochemical assay was used to examine GROs blockage of aggregation. Molecules T40216 (SEQ ID NO:2) and T30923 (SEQ ID NO:1), GROs that are known to form intermolecular G-quartets were found to be effective inhibitors of aggregation. Both of these GROs, adopt conventional G-quartet structure with the G residues (quartets) in the center and a loop domain at the top and bottom. The GROs of the invention, including the preferred HDG, which exhibits the highest level of activity in the aggregation assays, can also adopt a stable G-quartet structure and further studies to elucidate the details of the G-quartet structure adopted by HDG are currently being performed. This molecule of the invention also may prevent or delay neurotoxicity in PC12 cells.

In one of the embodiments, aptaperic GRO, HDG (SEQ ID NO:3), is unique among monotonic ODNs containing 20 bases. None of the related 20-mers, HDA, HDC or HDT (SEQ ID NOs: 8-10) show reproducible inhibitory activity in either the biochemical or cell-based assays. Furthermore, HDG displays a dose response with concentrations as low as 1 μM exhibiting substantial levels of aggregate reduction. For example, HDG is effective when added at the start of the Q58-Htn aggregation reaction but much less so when added after the process has begun. Without being limited to any particular theory, the inventors speculate that HGD is likely most effective at blocking the nucleation phase of aggregation rather than the elongation phase.

HDG (SEQ ID NO:3) was also found to be quite active in blocking aggregation of the Httexon1-eGFP fusion protein aggregation in HEK293 cells. In this system, the fusion protein is produced from an expression plasmid and co-transfection with HDG was found to prevent the appearance of green fluorescent foci in a dose-dependent inhibition. Importantly, the well-known aggregation inhibitor, Congo Red, was used as a positive control and displayed effects similar to HDG. MTT (3,[4,5-dimethylthiazol-2-yl]-2,5-diphenyltetrazolium bromide) viability assays reveal no cell toxicity or negative effects on cell growth as a function of ODN addition (data not shown). This result is not surprising since ODNs used as antisense or antigene therapy have been found to be practically inert in human cells with regard to cytotoxicity. A number of clinical trials using ODNs have taken place and while the efficacy of such treatments may be questioned, significant adverse effects on cells or patients were not observed. The lack of serious side effects from ODNs is a virtue in the development of these molecules for use in HD patients. For example, while the effective levels for GRO activity of the GROs of the present invention are higher than those used for traditional pharmaceuticals, ODNs are particularly well-tolerated in humans. The levels presented herein are not unusual and levels exceeding 50 mg/kg have been found to be both efficacious and nontoxic in various antisense therapies. The higher amounts may be required because delivery to target cells or penetration into the cells may be less efficient than other drug treatments.

Figure 11:
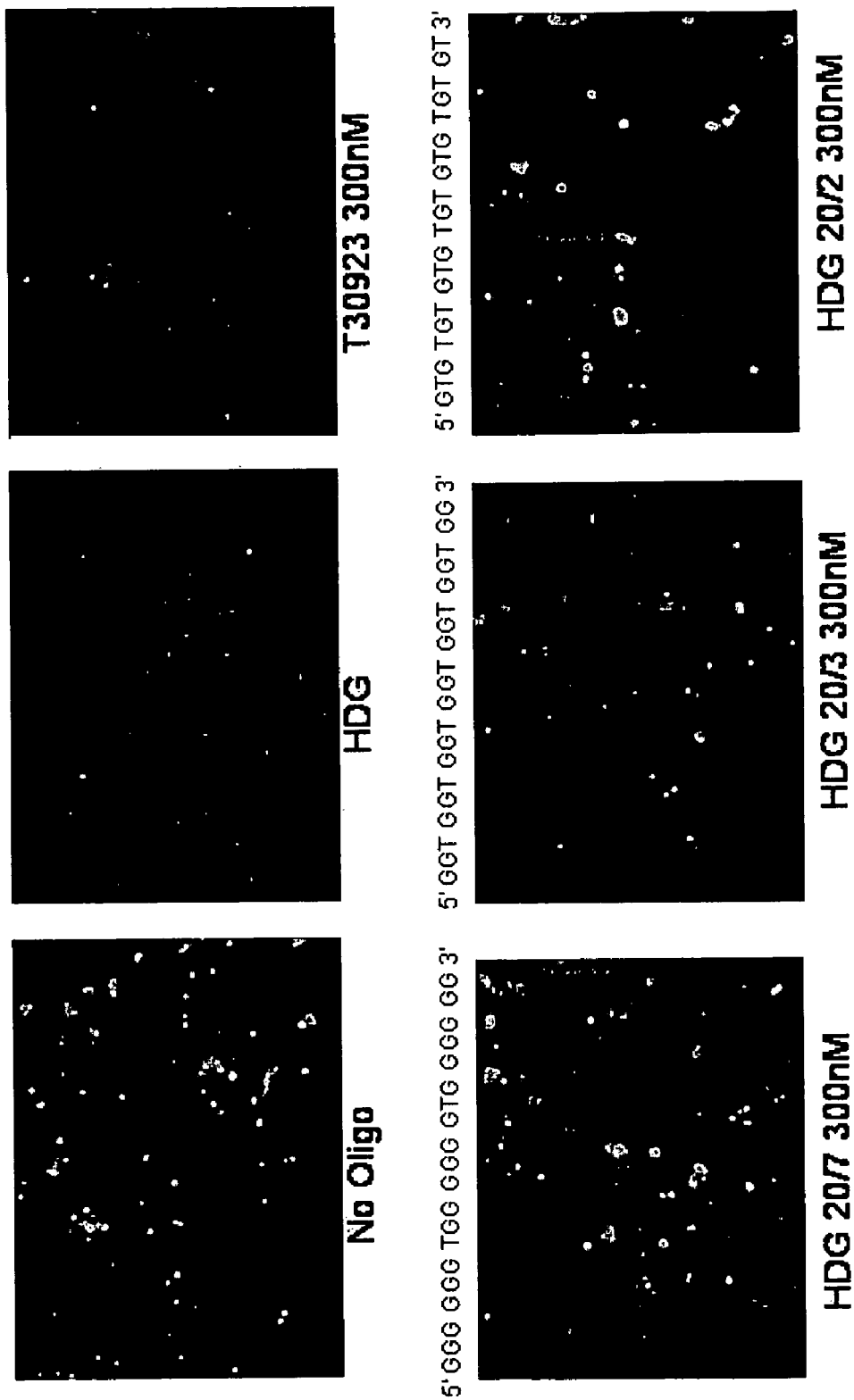
FIG. 11 provides dark field microscopic images showing HDG (SEQ ID NO:3) that was co-transfected with p72Q and the cells photographed 48 hours later under dark field. The upper left panel represents a reaction lacking ODN.

The aptameric GROs of the invention were modified in order to determine and confirm the potency of the G-quartet structure of the GROs, including HDG (SEQ ID NO:3). Using a type of reverse genetics strategy, we created several "mutant" HDGs; HDG 20/7 (SEQ ID NO:7) wherein each 7th G was replaced with a T, HDG 20/3 (SEQ ID NO:5) wherein each 3rd G was replaced with a T and HDG 20/2 (SEQ ID NO:4) wherein every other G was substituted with a T residue. None of these molecules were found to be effective inhibitors of aggregation. The results presented in FIG. 11 most clearly illustrate the importance of the HDG G-quartet structure while support for this notion is also gained when T30923 (SEQ ID NO:1) could not fully substitute for HDG in the HEK293 assay as presented in Example 3.

G-quartets formed within GROs have also been shown to inhibit protein dimerization of such molecules as STAT3. They exert their activity by binding to specific domains within STAT3 with a high degree of precision. Since mutant Htt aggregation relies on a nucleation phase in which the mutant protein begin to assemble, HDG (SEQ ID NO:3) could block the transition between nucleation and elongation as aggregation (dimerization) begins. Alternatively, HDG could block other enzymes involved in the development of the pathogenic phenotype, such as caspases which cleave the native protein perhaps producing a toxic fragment. Bates and colleagues have shown that certain aptameric GROs can bind to nucleolin in a variety of cancer cells with a high degree of specificity. In all of these cases, direct interactions with cellular proteins would be required.

As described above, we have shown that G-rich oligonucleotides, most preferably the HDG (SEQ ID NO:3) having a length of approximately 18-25 G-residues, and more preferably, 20 G residues, inhibits the aggregation process in a mutant Huntington protein. Functional ODNs which inhibit Huntington aggregation include the following aptameric GROs:

```
                                              (SEQ ID NO. 3)
HDG      5'-GGG GGG GGG GGG GGG GGG GG-3'

(SEQ ID NO. 11)
GRO26B 5'-GGT GGT GGT GGT TGT GGT GGT GGT GG-3'

(SEQ ID NO. 12)
GRO29A 5'-TTT GGT GGT GGT GGT TGT GGT GGT GGT GG-3'
```

In other aspects the present invention comprises a random screening process for finding active ODNs which inhibit protein aggregation. These G-rich ODNs (GROs) are known to possess aptameric activity, and we believe this aptameric activity is important for the non-specific binding of the ODN to the protein. GROs are capable of interacting with numerous cellular proteins owing to their polyanionic character or specific secondary structure. These aptameric GROs form quadruplex structures which are stabilized by G-quartets. We believe they have therapeutic potential for protein aggregation-related diseases. Current results show the level of aggregation is minimal compared to controls which contain no aptameric GRO and are normalized to 100% aggregation.

Although the invention is illustrated and described herein with reference to specific embodiments, the invention is not intended to be limited to the details shown. Rather, various modifications may be made in the details within the scope and range of equivalents of the claims and without departing from the invention.

EXPERIMENTAL EXAMPLES

Variations in the structure of the ODNs. The aptameric GRO molecule, HDG (SEQ ID NO:3), is 20 bases in length, and is composed of all G nucleotides. While it exhibits robust activity thus so far, we cannot assume that HDG is the most optimal vector. Thus, we changed HDG in a methodical fashion and tested variants in the biochemical screen. The chart below outlines strategic plans and the rationale for modifying HDG:

| | Variable | Specific Changes | Rationale |
|---|---|---|---|
| A. | Length | 20→18→16...4 bases, length are changed in steps of 2 | Shorter ODNs may be more capable transiting the BBB |
| B. | Composition | Guanosine DNA bases are tested first and 2'-O-methyl RNA bases (all G's) are tested in turn | RNA can adopt similar structural changes in tracts of G residues. 2'-O-methyl RNA is more stable than unmodified RNA |
| C. | Sequence | All G residue tracts are interrupted with Ts at various intervals i.e. GGGTGGGTGGGT etc. | G-quartet structures are also known to form with T residues at $3^{rd}$ and $4^{th}$ positions: some with greater stability |
| D. | Chemical Modifications | G residues are linked with phosphodiester bonds. HDG is changed to contain LNA, or PNA bases and/or phosphorothioate linkages (PS) | LNA or PNA bases may assist in crossing the BBB more readily and phosphorothioate linkages protect against nuclease digestion |

Each of these alterations was evaluated for biological activity using a matrix of conditions, but, the primary discriminatory screen involved length since eventually smaller molecules will be more likely to penetrate the BBB (see below). Once several short active molecules were identified, other modifications were tested, including the incorporation of T residues into the G-rich sequence, linkage groups and base chemistries. As a standard, however, HDG was processed through all of the assays. The most active GROs were analyzed in time-of-addition experiments wherein the ODN was added at periodic intervals following the initialization of protein aggregation.

Active GROs and/or related GROs that were identified were re-screened at various dosages in a range of 10-2 μM through 102 μM to generate an IC50. Each assay group was tested in triplicate with the blots scanned and quantitated using Image Quant Software. Of particular interest were GROs with PNA linkages because of their potential advantage in crossing the BBB. We focused on synthesizing GROs with various number of PNAs and conducted a methodical, systematic analyses of PNA (and LNA)-modified GROs. The baseline for all assays was established using two control samples; Congo Red and I to set positive and negative boundaries. These control samples have been used routinely in previous screens and have proven to be quite robust in establishing the parameters and validating the assay system. IC50 was obtained by graphing the % aggregate reduction and the concentration (μM) on a log scale. Standard deviation, SEM means and P values will be automatically calculated for each point using a program from Prism 3.0 software, one way ANNOVA and Tukey's posttest for multiple comparisons, respectively.

Structural analyses of G-rich ODNs exhibiting inhibitory activity: structure/function relationships. GROs are believed to fold into a stable (G-quartet) secondary structure. G-quartets are formed between the N1 to O6 and N2 to N7 positions of adjacent guanosines; such interactions, amid a string of Gs which stack in a coordinated fashion giving rise to tetrad helices. Secondary structures form under favorable ionic conditions that include an environment rich in K+ ions; but can form in the presence of other monovalent cations. Importantly, the cellular concentration of KCl is 140 mM, clearly above the required minimum concentration conducive for G-quartet assembly.

We analyzed the structure of each GRO that exhibited significant activity in the biochemical assay. Circular dichroism was used to analyze structure including HDG (SEQ ID NO:3) at a concentration of 15 μM in 10 μM KCl and 20 mM Li3PO4 at pH7 at 24° C. The spectrophotometer used was a JASCO J-500A spectropolarimeter which allowed us to obtain data in molar ellipticity (deg.cm2dmol-1). For each ODN, we utilized 5-10 scans and integrated all scans to determine the most probable structural profile. The GROs were synthesized by Integrated DNA Technologies (IDT, Coralville, Iowa) and quantitated by the manufacture. GROs were tested at 264 nm with a minimum of 240 nm as ellipticities at 264 nm and 240 nm respectively are highly characteristic of a G-quartet structure. The following ODNs which are known to form these structures were used as positive controls: T30923 (SEQ ID NO:1), 5'-GGGTGGGTGGGTGGGT-3', and T40216 (SEQ ID NO:2), 5'-GGGGGTGGGGGTGGGGTGGGGGT-3'. For negative controls, the following ODNs, which have are known not to form a G-quartet, NS-ODN, 5'-TGCCGGATCAAGCGC-TACCA-3' and the poly A monomer of 20 bases in length, HDA (SEQ ID NO:9), were utilized. By generating CD spectra profiles of the G-quartets, with GROs known to adopt that structure we were able to compare and even correlate our candidate GROs exhibiting strong activity in the aggregation assays with the degree of G-quartet formation. By coupling this information we were able to gain some fundamental insight into the structure of the efficacious molecules.

Structure/function analyses were also be carried out using PAGE. In this assay, G-rich ODNs were electrophoresed through a 19% native acrylamide gel matrix and stained with SYBR Gold, a protocol that enables visualization of the degree of secondary structure in the sample. Such a procedure is most useful in analyzing potential variation that could occur among preparations of GROs obtained from the manufacturer. It does not, however, measure G-quartet assembly. We also compared GROs that exhibit high levels of activity to those that do not, with a goal correlating secondary structure with increased or decreased levels of inhibitory activity, with the long term goal of identifying a "structural marker" for active GROs. Secondary structures were detected and quantified after staining with a Typhoon Image using a 532 nm green filter directly from the imaged gel.

Example 2

Biochemical analyses of GROs. We chose to utilize a biochemical/immunochemical assay system that enables rapid screening of compounds/molecules for the inhibition of aggregation. In this test, ODNs were mixed with purified mutant Htt fragment for 24 hours and then passed through a cellulose acetate membrane filter. The percentage of aggregates remaining on the filter was detected by immunochemistry using a primary Htt-antibody and a secondary anti-rabbit antibody conjugated to peroxidase. Signals from the SDS insoluble aggregates were scanned and quantified. A diagram of this assay, established by Wang et al. (2005), is presented in FIG. 1. In all preparations of the mutant protein, thrombin-directed cleavage of GST-Q58Htn was allowed to proceed for 45 minutes prior to the addition of the GRO. This cleavage generates an amino terminal polyglutamine fragment consisting of 171 amino acids of the human huntingtin with tract of 58 glutamine residues. The fragment is fused to GST to enable purification. We will utilize the Wang et al terminology, GST-Q58-Htn to designate the protein used in this assay. The mixture was centrifuged to remove any aggregates that had already formed. Western blot analyses have shown that >95% of the GST-Q58-Htn is cleaved to completion by the thrombin. This parameter is an important control for our study since a variety of agents are known to block the enzymatic cleavage reaction directed by thrombin.

Two known GROs were tested for inhibitory activity in the biochemical assay described above. ODN T30923 (SEQ ID NO:1) and ODN T40216 (SEQ ID NO:2) were used as aptamers to inhibit the function of STAT3 protein. Both of these molecules have been determined by Circular Dichroism (CD) and NMR to have an intramolecular G-quartet structure, and similar CD spectra were seen by our lab (see below). The sequence of each is provided in FIG. 2A; T30923 contains $(GGGT)_4$, 16 bases in length while T40216 contains $(GGGGGT)_4$, 24 bases in length.

To analyze the inhibition of aggregation by GROs, a biochemical assay was employed (FIG. 1). The fusion protein GST-Q58-Htn was incubated for 45 minutes at room temperature with thrombin (1 U/1 µg protein) at a concentration of 10 µg/ml in a buffer of 50 mM Tris-HCl, pH 8, 100 mM NaCl, 2.5 mM $CaCl_2$, and 1 mM EDTA, to cleave between the huntingtin and GST. As indicated by Wang et al., this fragment consists of the amino terminal 171 amino acids with a tract of 58 glutamine residues fused to GST. The protein mix was then centrifuged at 30,000×g at 4° C. for 35 minutes to remove any aggregates that had already formed. The protein was added to wells containing 0.5-60 µM GROs or control ODNs, 10 µM Congo Red, or no treatment in the buffer detailed above with 100 mM KCl replacing NaCl. The 0-hour control was stopped immediately and after 24 hours incubation at room temperature the remaining reactions were stopped by adding 10% SDS/50 mM 2-mercaptoethanol and heating to 99° C. for five minutes. The mixture was diluted in 1× PBS and then filtered through a cellulose acetate membrane (Osmonics) using the Easy-Titer ELIFA system (Pierce) followed by a 2% SDS wash. After blocking in 5% milk/1× PBS-0.05% Tween, the membrane was incubated with a specific anti-huntingtin antibody (HP1, 1:1000 dilution), followed by incubation with a peroxidase-conjugated goat anti-rabbit antibody (Sigma, 1:40,000 dilution) and chemiluminescence reagent (ECL-Plus, Amersham). Signals from the aggregates retained on the filter were scanned and quantified using ImageQuant image analysis software (Molecular Dynamics). Aggregates were quantified by optical density and statistical differences were determined by one way ANOVA with Tukey's post hoc analysis using Statistical Package for the Social Sciences (SPSS). Significance was determined by a $p<0.05$ as compared to Congo Red (control).

Figure 2:
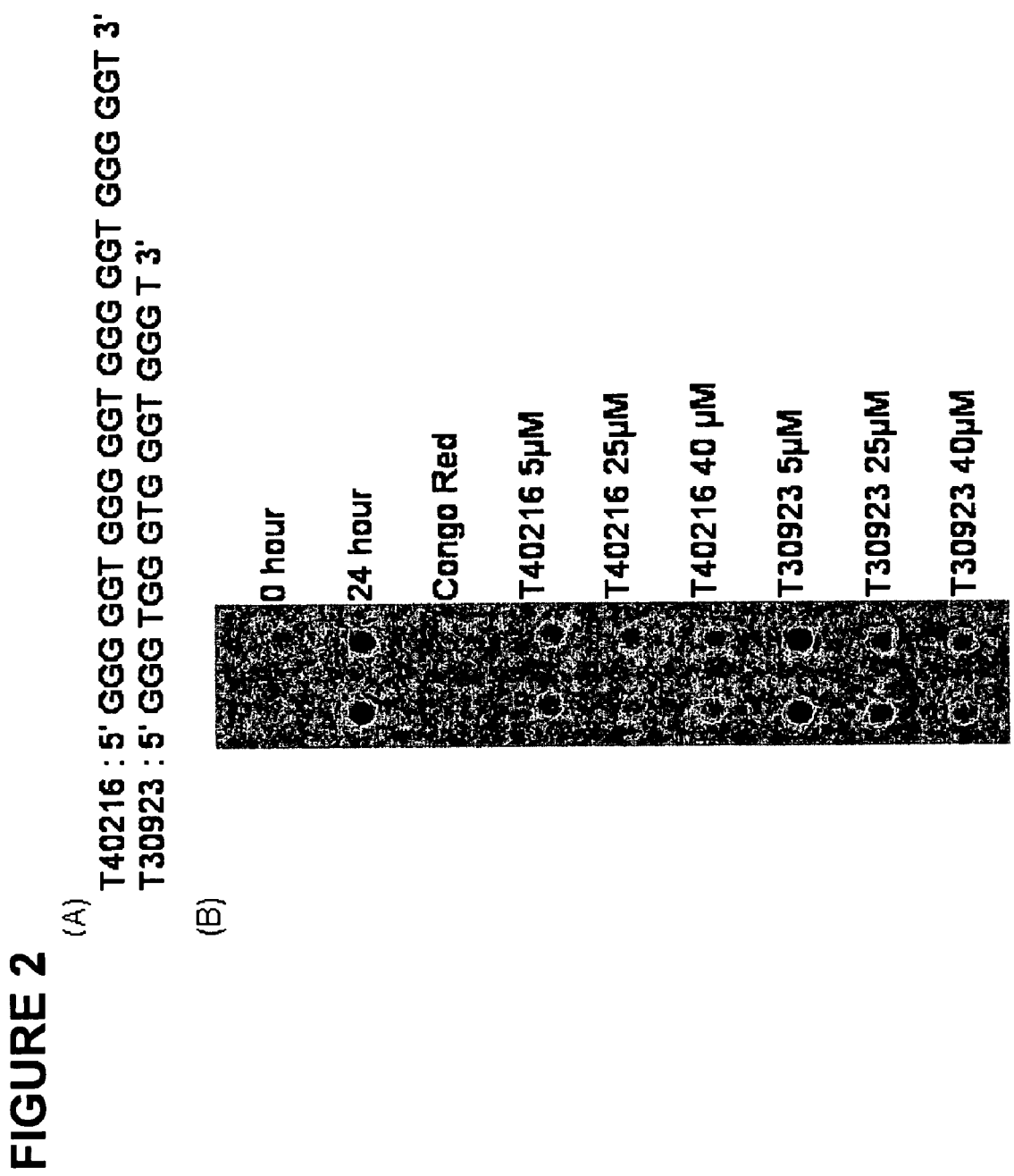
FIG. 2 (A) is the DNA sequence of two G-rich ODNs that form the G-quartet structure (SEQ ID NOs: 1 and 2). (B) is a dot blot analysis of T40216 (SEQ ID NO:2) and T30923 (SEQ ID NO:1) activity on aggregation. The zero (0) hour control represents reactions that were stopped immediately after addition of the protein; 24-hour reactions carried out in the absence of the ODN and stopped after 24-hours of incubation; Congo red, level of aggregation 24 hours after addition of Congo Red (10 μM).
Figure 3:
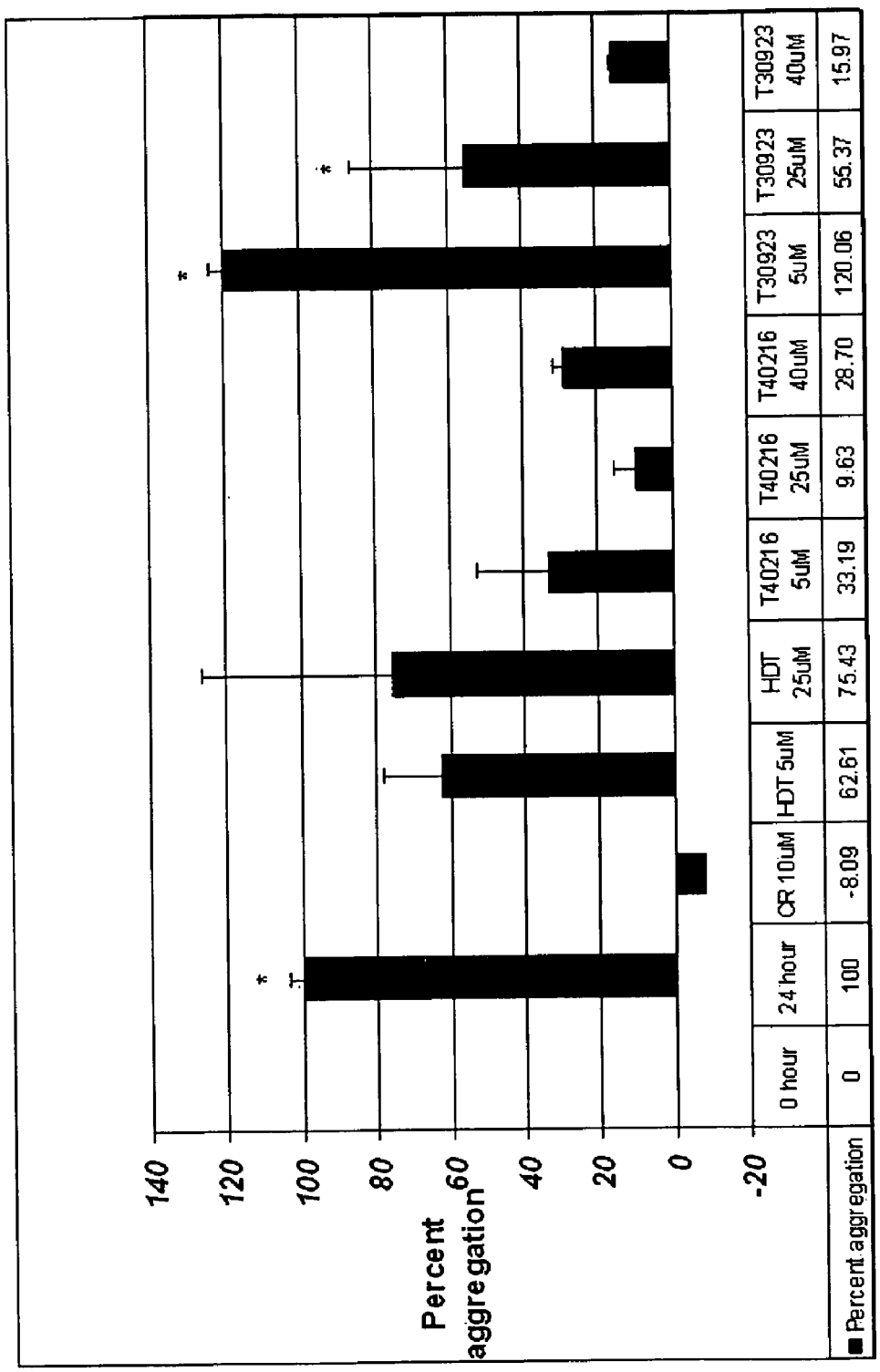
FIG. 3 is a bar graph depicting aggregation inhibition by GROs. Here, T40216 (SEQ ID NO:2) and T30923 (SEQ ID NO:1) and Congo Red are used: Data are presented from five independent reactions, as shown in (B) for each point with standard deviation. *, denotes significance $p<0.05$ as compared to Congo Red (control) as determined by a one way ANOVA with Tukey's post hoc test.

Three control reactions, designated 0-hour, 24-hour and Congo Red (FIG. 2B), were repeated for each experiment. The 0-hour control displays the amount of aggregation at the start of the reaction, usually none. The 24-hour control reflects the amount of GST-Q58-Htn aggregation when no inhibitor is added to the mixture. The third control displays the degree of aggregation formed in the presence of Congo Red, a known inhibitor functioning as the positive control in the series. As shown in FIG. 2B, both T40216 (SEQ ID NO:2) and T30923 (SEQ ID NO:1) are capable of inhibiting GST-Q58-Htn aggregation with a dose response visible in the samples with T30923. FIG. 3 represents the results of five experiments conducted in duplicate, followed by quantitation using ImageQuant analytical software. A statistically significant difference is observed between each GRO and the 24-hour control in each experiment.

Figure 5:
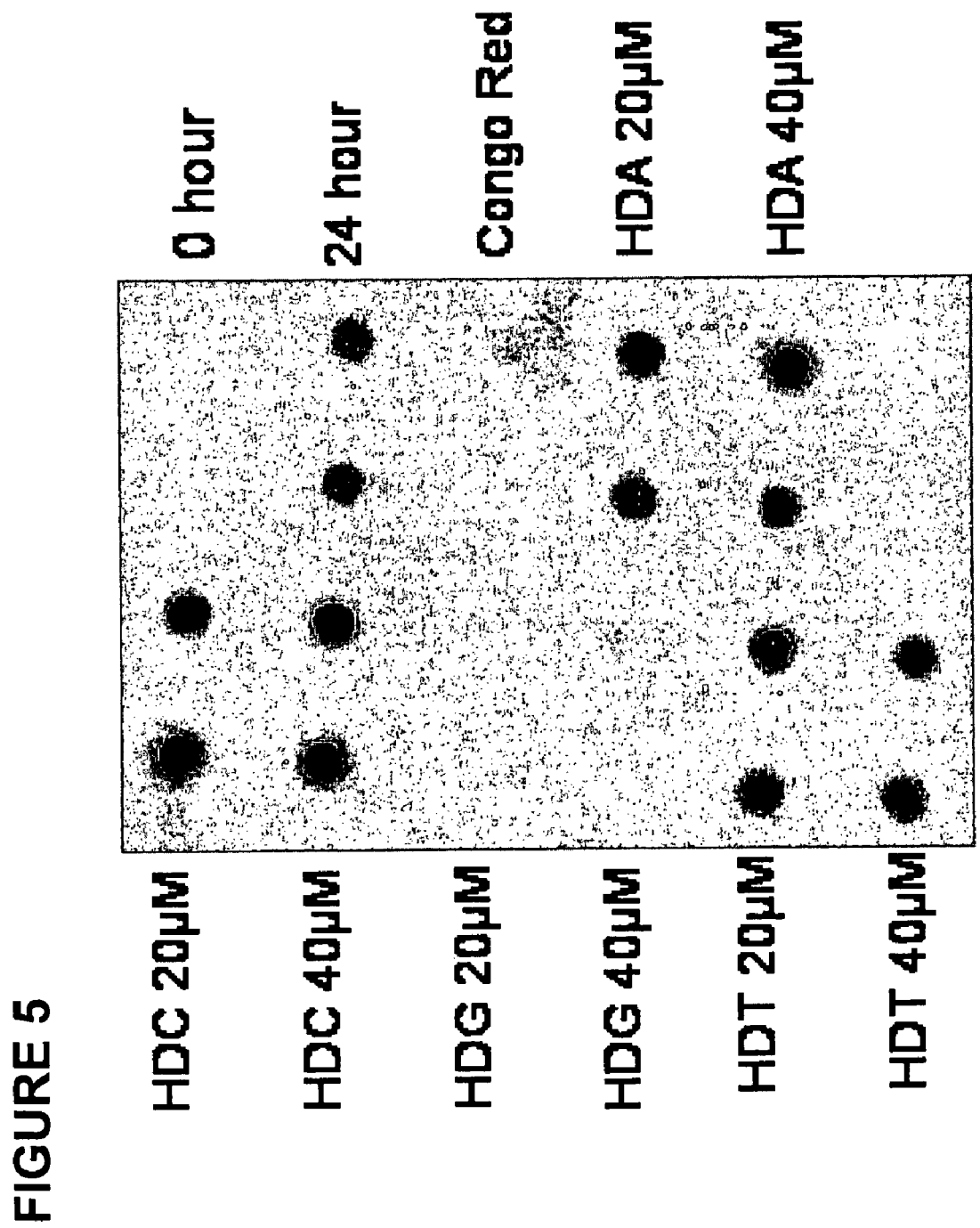
FIG. 5 is a dot blot analysis of the specificity of various monotonic 20-mer ODNs in the inhibition of mutant Htt fragment aggregation. The various monotonic 20-mers were tested for inhibitory activity in the assay outlined in FIG. 1. HDC, 20-mer with all Cs (SEQ ID NO:8); HDA, 20-mer with all As (SEQ ID NO:9); HDT (SEQ ID NO:10), 20-mer with all T's; HDG, 20-mer with all Gs (SEQ ID NO:3). Four independent experiments were carried out in duplicate and this blot is most representative of all of the results. 0 hour, reaction stopped at zero time point; 24 hour, reaction lacking ODNs, stopped at 24 hours; Congo Red, incubation with 10 µM of Congo Red for 24 hours.

The effect of GROs on aggregation prompted an examination of the activity of a monotonic guanosine ODN (HDG; SEQ ID NO:3) because this molecule can also form a G-quartet. We chose 20 bases as a compromised length of T30923 (SEQ ID NO:1) (16 bases) and T40216 (SEQ ID NO:2) (24 bases) to establish the HDG series. When a dose range of HDG was tested in the biochemical assay, inhibition of aggregation Q58-Htn fragment was readily observed (FIG. 4). A significant decrease was seen at 1 µM, a much lower final concentration than the inhibitory level found with either T30923 or T40216. HDG was found to be unique in its inhibitory activity compared to other monotonic ODNs. Huang et al. demonstrated that the flow-through fraction of reactions containing inhibitors of aggregation is comprised predominantly of monomeric Htt fragments. To verify that the flow-through in reactions bearing HDG 20 contains mutant Htt fragments, we captured this fraction and placed it on blotting paper. Stacked membranes to capture monomers using the same antibody used to detect aggregates. As seen in the inset for FIG. 4, a positive reaction was observed indicating the presence of mutant Htt fragment. When 20-mers of A (HDA; SEQ ID NO:9), T (HDT; SEQ ID NO:10) or C (HDC; SEQ ID NO:8) were tested at 20 µM and 40 µM, no inhibition of aggregation was observed (FIG. 5). Quantitation after scanning revealed a large, statistically significant difference in the activity of HDG compared to any of the other monotonic ODNs (FIG. 6). Taken together, our results suggest that HDG, a 20-mer containing all G residues, is a powerful inhibitor of aggregation of Q58-Htn fragment based on the results of the immunoblotting assay.

Figure 7:
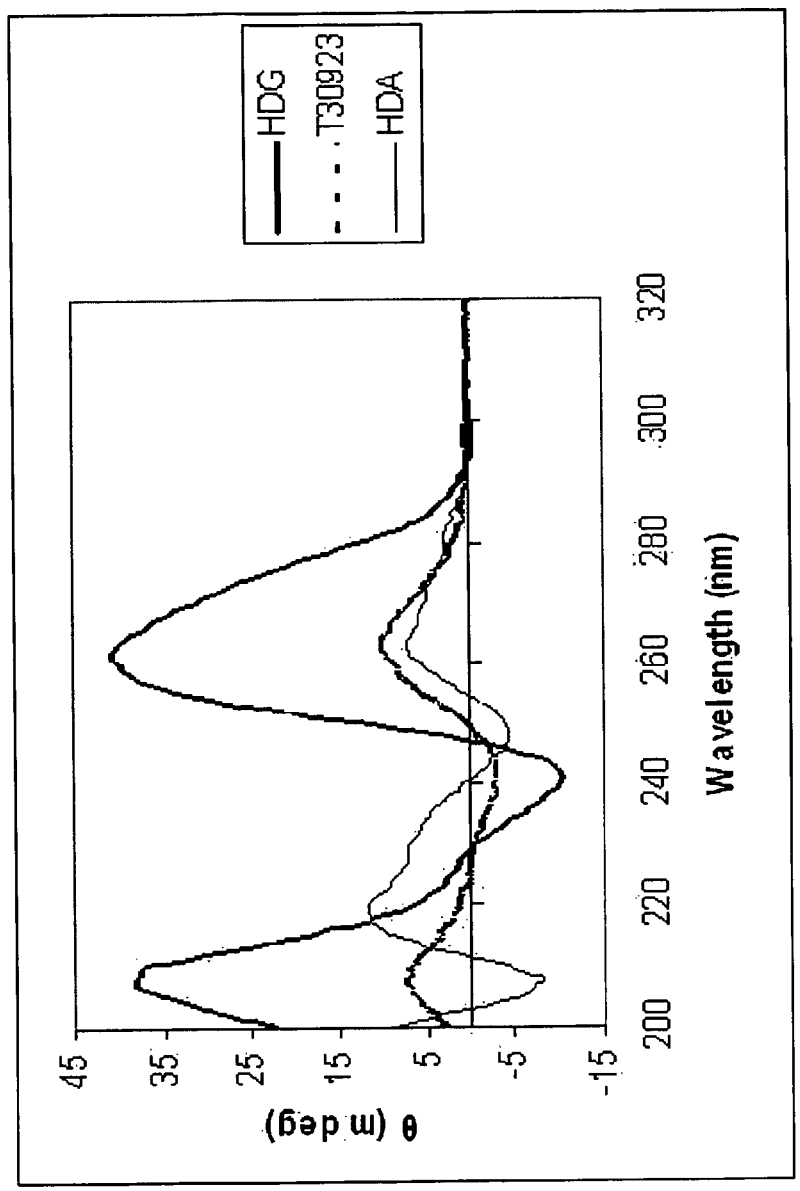
FIG. 7 is a CD spectroscopy of HDA (SEQ ID NO:9) and HDG (SEQ ID NO:3). The CD spectra of 15 µM HDG (heavy solid line), 15 µM T30923 (SEQ ID NO:1) (light solid line) and 15 µM HDA (dotted line) in 10 mM KCl at 24° C.

CD measures differences in the absorbance of right-handed and left-handed circularly polarized light and can be used to investigate DNA helicity. G-quadruplexes can exist as antiparallel monomers, dimers or tetramers or as parallel tetramers. Traditionally, antiparallel conformations are characterized by a positive ellipticity maximum at 295 nm and a negative minimum at 265 nm. In contrast, the parallel conformation is characterized by a positive maximum at 264 nm and a negative minimum at 240 nm; however, recent results have shown some antiparallel structures to have some positive maximums at 264 nm and negative minimums at 240 nm. HDG (SEQ ID NO:3) was characterized by CD in order to gain a perspective view of its structure. HDG was analyzed along with HDA (SEQ ID NO:9) and T30923 (SEQ ID NO:1) at 15 µM in 10 mM KCl and at 24° C. CD spectropolarity was determined using an AVIV Model 202 spectrometer with an effective range of analysis from 200 nm to 320 nm (FIG. 7). HDA has an unusual maximum absorbance at 220 nm with a smaller positive absorbance at 260 nm. T30923 and HDG, however, exhibit maximum positive absorbances at 264 nm and negative minimums at 241 nm, a distinct profile that matches closely with molecules known to adopt G-quartet structures. HDG is a more effective inhibitor of GST-Q58-Htn aggregation than T30923 which is known to adopt a dimer basket G-quartet conformation [see 7] suggesting that HDG's structure is a more active conformation in our assays.

Example 3

Figure 8:
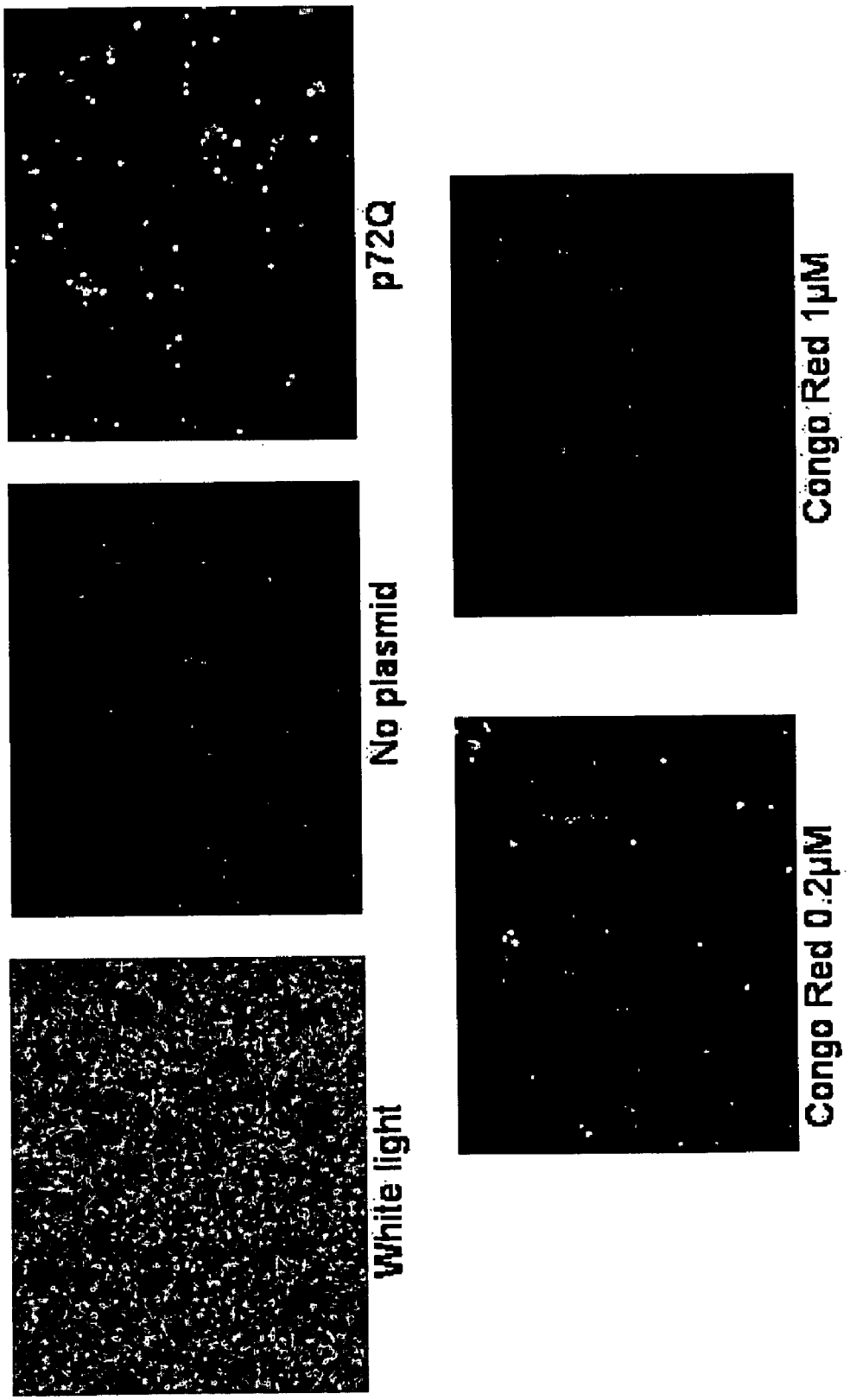
FIG. 8 provides light and dark field microscopic images showing inhibition of aggregation in HEK 293 cells transfected with plasmid, pcDNA3.1-72Httexon1-eGFP (p72Q). Series of control reactions including HEK293 photographed under white light or in dark field, aggregate formation produced by p72Q and inhibition of aggregation by Congo red (0.2 µM or 1 µM) added concurrently with p72Q.
Figure 9:
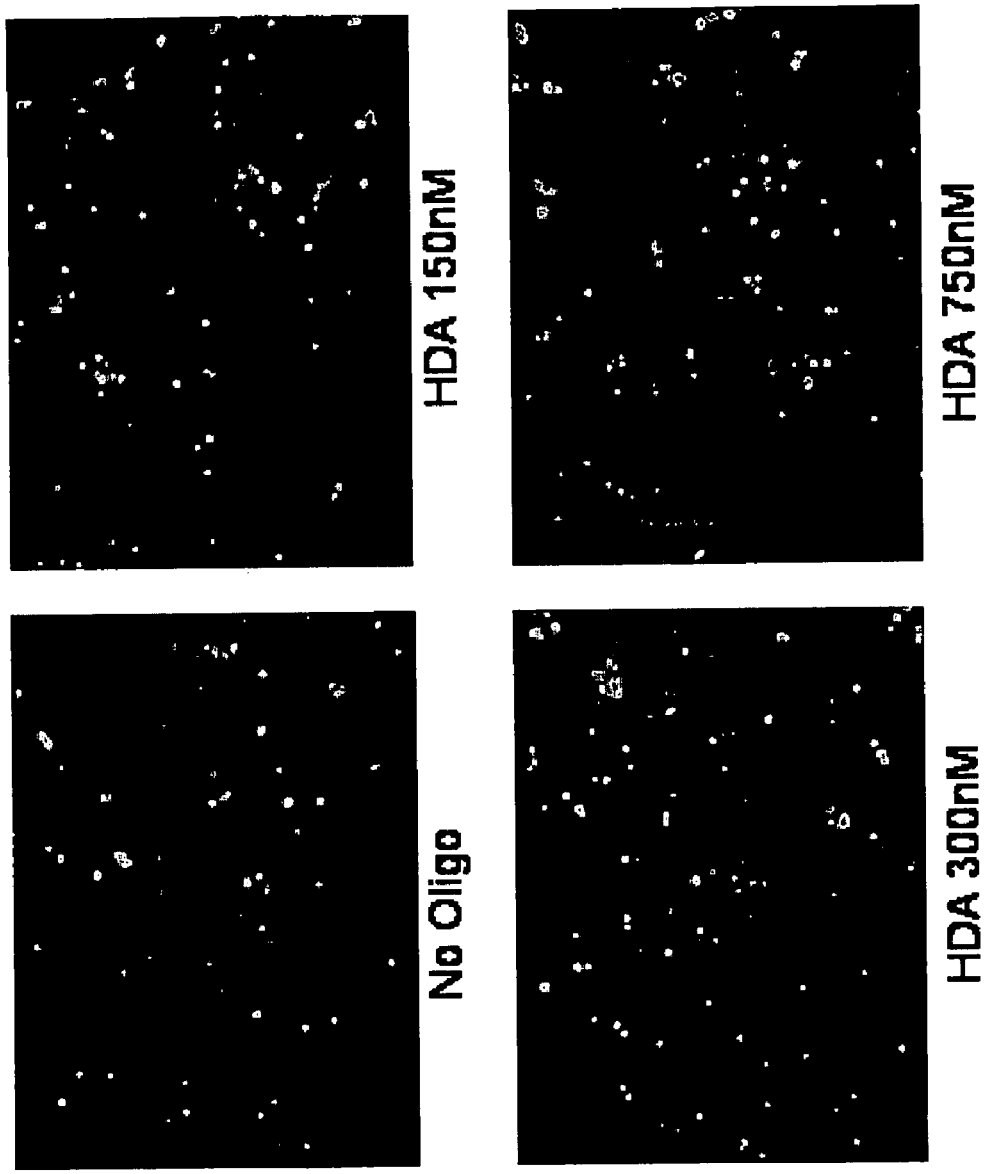
FIG. 9 provides dark field microscopic images showing HDA (SEQ ID NO:9) that was co-transfected at the indicated concentrations with p72Q and the cells were photographed 48 hours later in dark field.
Figure 10:
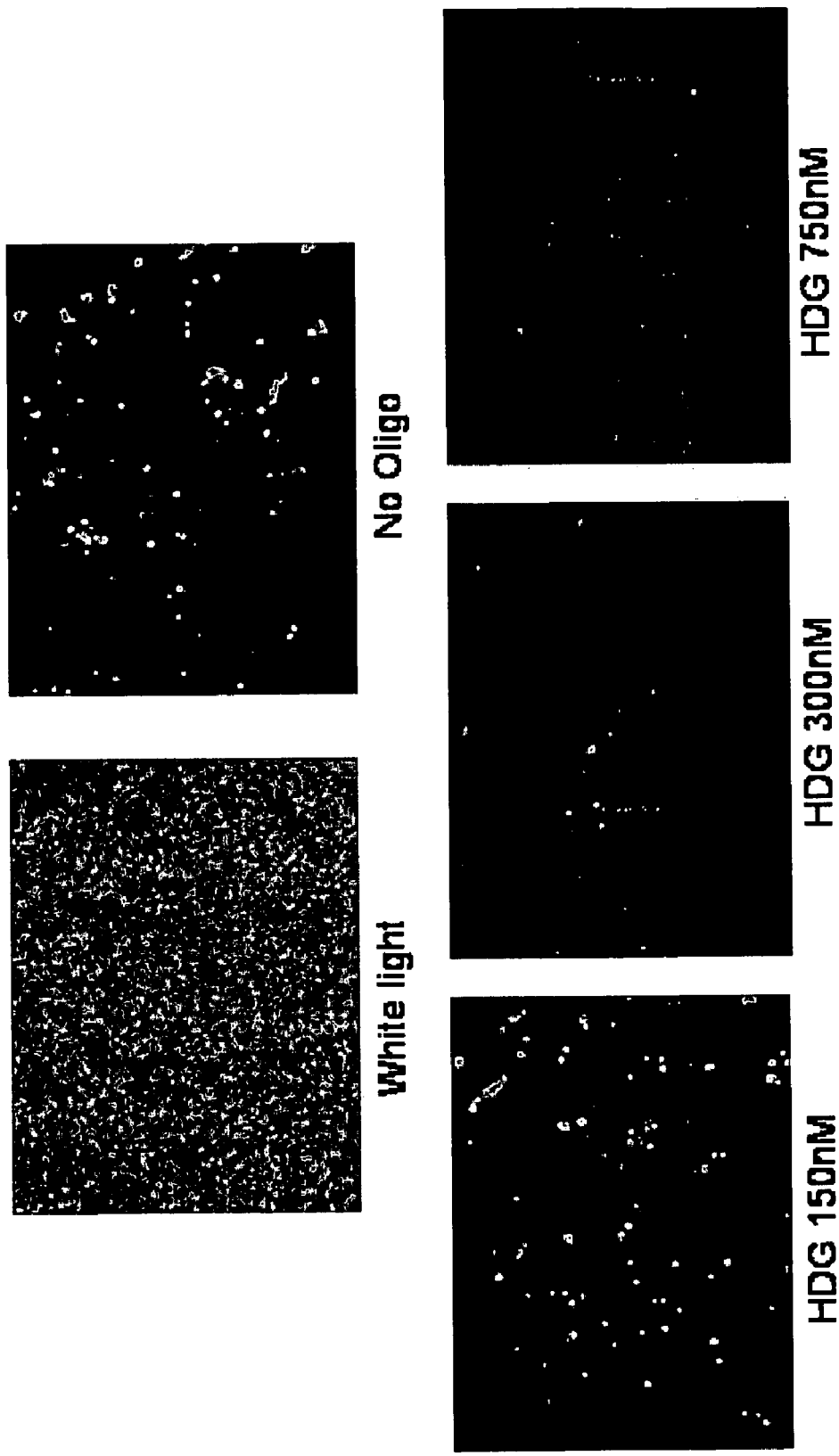
FIG. 10 provides light and dark field microscopic images showing HDG (SEQ ID NO:3) that was co-transfected at the indicated concentrations with p72Q and the cells were photographed 48 hours later in dark field.
Figure 12:
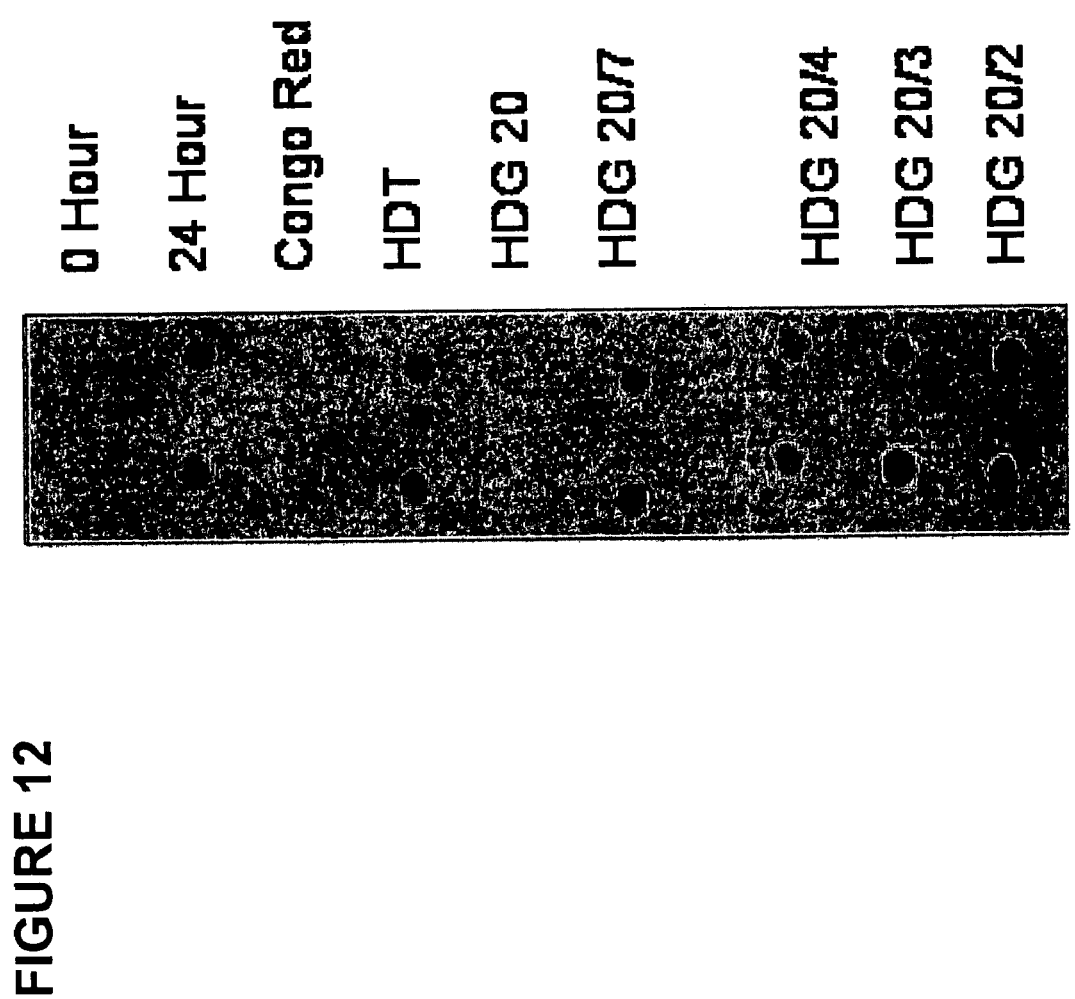
FIG. 12 is a dot blot analysis of various 20-mers having thymine modifications were tested for inhibitory activity in the assay outlined in FIG. 1. HDT (SEQ ID NO:10), 20-mer with all T's; HDG (SEQ ID NO:3), 20-mer with all G's; HDG 20/7 (SEQ ID NO:7), 20-mer with every 7th nucleotide replaced with T; HDG 20/4 (SEQ ID NO:6), 20-mer with every 4th nucleotide replaced with T HDG 20/3 (SEQ ID NO:5), 20-mer with every 3rd nucleotide replaced with T; HDG 20/2 (SEQ ID NO:2), 20-mer with every other nucleotide replaced with T. 0 hour, reaction stopped at zero time point; 24 hour, reaction lacking ODN and reaction stopped at 24 hours; Congo Red, incubation with Congo Red (10 µM) for 24 hours.

Inhibition of aggregate formation in HEK293 cells. Since HDG (SEQ ID NO:3) exhibited strong inhibitory activity of GST-Q58-Htn in a biochemical assay, we tested this molecule in a cell-based assay. Human embryonic kidney cells, HEK293T, were grown in low glucose DMEM supplemented with 10% FBS. Cells were seeded at 0.5-1×106 cells/well on 6-well plates. The cells were transfected with 1 µg of the plasmid pcDNA3.1-72Httexon1-eGFP (p72Q) and 150-750 nM GRO or control ODN using 2.5 µl Lipofectamine 2000 (Invitrogen). Forty-eight hours after transfection cells were viewed to determine the approximate number of green fluorescent foci using an Olympus IX50 microscope. pcDNA3.1-72Httexon1-eGFP (p72Q) is a construct that contains a fusion gene uniting the first exon of the HD gene containing a polyQ repeat of 72 codons and the eGFP gene. This fragment of huntingtin differs from GST-Q58-Htn in both length of polyglutamine stretch and that it is fused to eGFP rather than GST. When transfected into HEK293 cells, the gene is expressed and aggregates appear within 12 hours, reflected by the appearance of discrete green foci. Cells were photographed first under white light to verify that equal numbers of cells were present for each treatment and a representative sample is shown. eGFP foci were then imaged in the presence or absence of plasmid p72Q. In FIG. 8, green fluorescent foci are evident when p72Q is present but a significant reduction is seen in cells that have also received Congo Red. Importantly, inhibition of aggregate formation is only partially inhibited when a lower dosage of Congo Red is present, demonstrating a dose-dependent effect. In FIG. 9, a cell population in which HDA (SEQ ID NO:9) was co-transfected with p72Q is presented; HDA appears to have had little effect on the number of aggregates formed in these cells. As is the case in the biochemical assay (FIG. 5), HDA does not appear to inhibit aggregate formation in HEK293 cells. FIG. 10 illustrates the effect of HDG on aggregate formation. The white light photograph again reveals that HDG has no detectable toxic effect on cells or cell growth at 750 nM (top left panel), but a clear dose effect is seen on the number of aggregates when the level of HDG is increased (bottom panels). These observations confirm results obtained in the biochemical assay using HDG as the inhibitor. Finally, in FIG. 11, a panel of photographs reveals once again that HDG is an effective inhibitor of aggregate formation but that this positive activity can be reduced significantly when T residues are inserted at the 7th and 14th position of the HDG 20-mer (HDG 20/7; SEQ ID NO:7), every third base of the HDG 20-mer (HDG 20/3; SEQ ID NO:5) or every other base of the HDG 20-mer (HDG 20/2; SEQ ID NO:4). To validate these results and to further explore the relationship between the cell-based, and biochemical assays, we assayed HDG 20/7, HDG 20/4 and HDG 20/3 individually for activity in the immunoblot assay (see FIG. 2B). These results confirm the low level of activity observed for HDG 20/7, HDG 20/3 and HDG 20/2 respectively in the cell-based assay (FIG. 12). The correlation between the results obtained in the cell-based and immunoblot assay reveal a similar mode of action for the ODNs. We have preliminary evidence that the reduction in aggregates observed in the cell-based assay can be confirmed when aggregates isolated from transfected cells are passed through the immunoblot assay.

Figure 13:
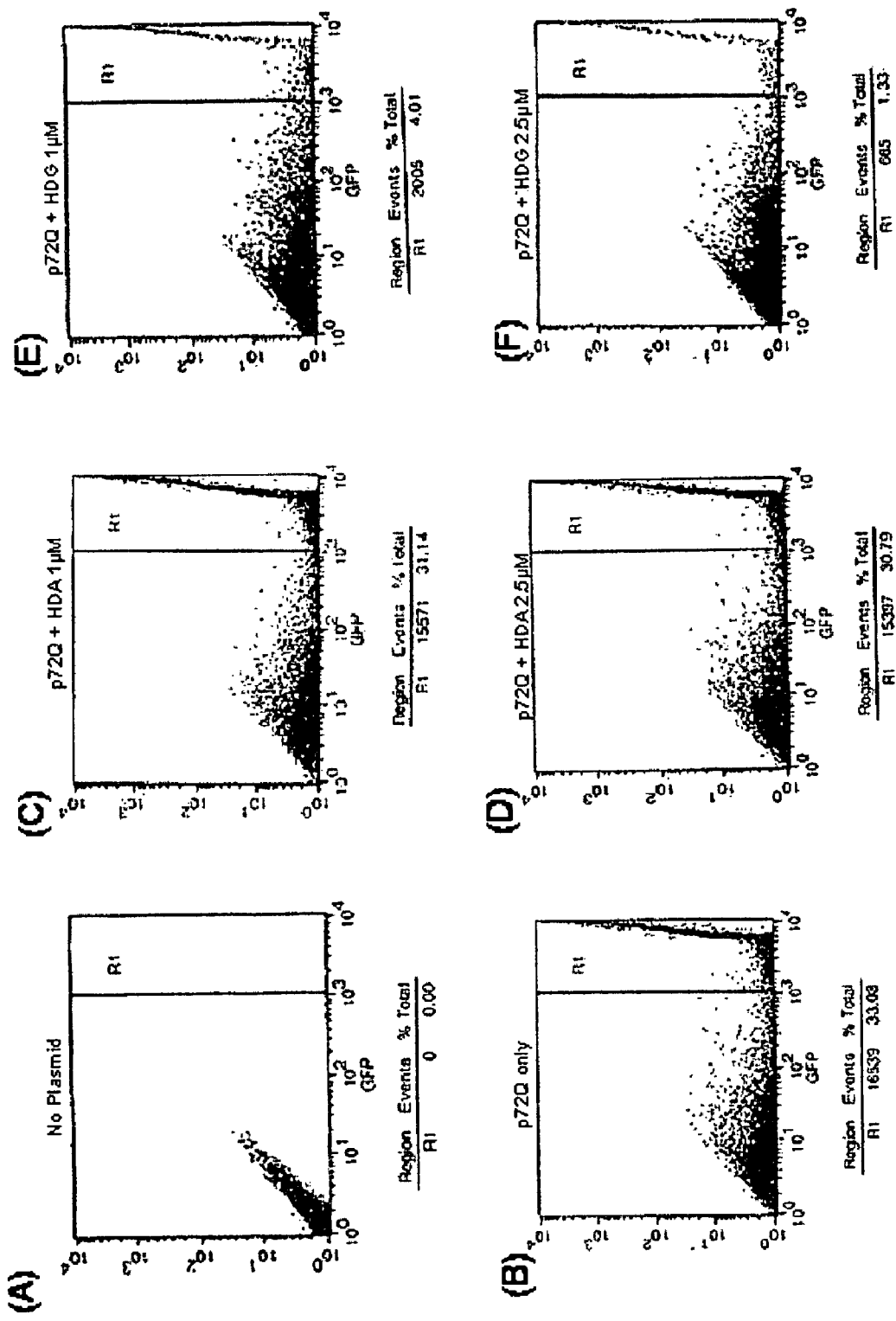
FIG. 13 is a FACS measured analysis of inhibition of mutant Htt fragment aggregation by various ODNs. HEK293 cells were transfected with pcDNA3.1-72Httexon1-eGFP (p72Q) and the specific ODN (HDA (SEQ ID NO:9), HDG (SEQ ID NO:3)) at the indicated concentrations and the degree of aggregation measured by FACS after 48 hours. (A) No plasmid (p72Q); (B) only p72Q, no ODN; (C) p72Q and 1 µM HDA; (D) p72Q and 2.5 µM HDA; (E) p72Q and 1 µM HDG; (F) p72Q and 2.5 µM HDG. All ODNs are at final concentrations in the cell culture reaction. The magnitude of green fluorescence is measured on the X axis while the number of cells exhibiting that degree of fluorescence is depicted on the Y axis.

Aggregate reduction in response to the addition of HDG (SEQ ID NO:3) can also be seen using FACS analysis as the readout. Again, HEK293 cells were transfected with p72Q with or without HDG (or HDA; SEQ ID NO:9) and the reactions were allowed to proceed for 48 hours. The cells were then processed for FACS and measured for green fluorescence. The Y axis reflects the degree or intensity of fluorescence. As seen in FIG. 13A, the background is gated at the far left of the graphic whereas expression of p72Q produces a sharp peak of green fluorescence near the right edge of the profile (FIG. 13B). This peak represents aggregated Htt-eGFP, scored by FACS as cells containing high intensity eGFP (aggregates). In FIGS. 13C and 13D, the profile of cells treated with HDA is represented and little detectable change is observed in the peak at the far right edge. Even as the level of HDA is increased from 1 µM to 2.5 µM, no significant reduction in aggregates is observed. In contrast, cells treated with HDG exhibit a very different profile (FIGS. 13E and 13F) as the peak representing aggregates is diminished in a dose-dependent fashion. Thus, taken together, the data suggest that HDG can inhibit aggregation formation in HEK293 cells expressing the Htt-eGFP fusion protein from plasmid p72Q.

Finally, a derivative PC12 cell line, Htt14A2.6, was used to measure the capacity of HDG to improve cellular viability. This neuronal cell line is used as a standard in the field for studying the survival phenotype associated with aggregate formation. In this assay, a truncated form of Htt exon 1 (103Q) fused to enhanced green fluorescent protein (eGFP) is induced to express by addition of muristerone to the culture.

Figure 14:
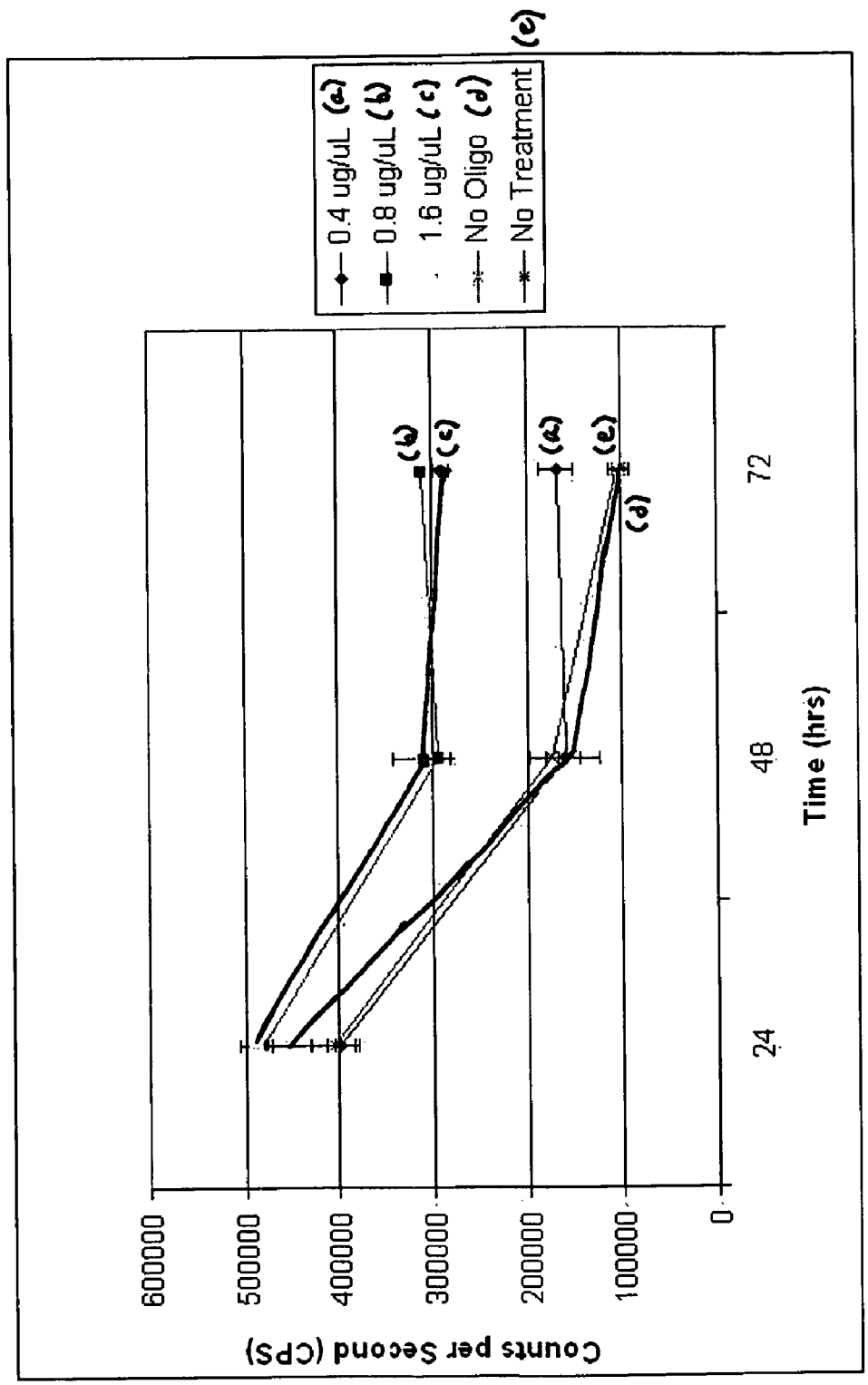
FIG. 14 is a line graph showing the viability of PC12 cells transfected with various HDG (SEQ ID NO:3) concentrations. The PC12 cell line, Htt14A2.6, was transfected with varying amounts of HDG in Lipofectamine 2000. The Promega CellTiter-Glo Luminescent cell viability assay was used to analyze the viability of each treatment as a function of time. One control is a mock-transfected cell culture containing lipofectamine 2000 but no ODN; whereas the no treatment control presented here indicates cells that have received neither ODN nor lipofectamine. Statistics were performed by using the standard deviation on 27 luminescent readings for every sample at each time point.

After induction, cell viability decreases rapidly between 48 hours and 72 hours, respectively, as measured by a CellTiter-Glo Luminescent cell viability assay, as shown in FIG. 14. The addition of increasing doses of HDG (SEQ ID NO:3) (0.4-1.6 µg/µl) appears to arrest the drop in viability providing some level of neuroprotection. The differences in these are statistically significant and a larger, survival study is underway to confirm and/or expand upon these results.

Circular dichroism spectroscopy. Circular dichroism spectra of 15 µM ODN samples in 10 mM KCl were recorded on an Aviv model 202 spectrometer. Measurements were performed at 24° C. using a 0.1 cm path-length quartz cuvette (Hellma). The CD spectra were obtained by taking the average of two scans made at 1 nm intervals from 200 to 320 nm and subtracting the baseline value corresponding to that of buffer alone. Spectral data are expressed in units of millidegree.

PC12 viability assay. Rat pheochromocytoma cells, PC12, were grown in high glucose DMEM with 10% horse serum and 5% FBS while under selection with G418 (0.05 mg/mL) and Zeocin (0.1 mg/mL) (Invitrogen). This cell line, Htt14A2.6, expresses a truncated form of expanded repeat Htt exon 1 protein containing 1-17 amino acids and 103 polyglutamine tract fused to eGFP. The promoter was induced with muristerone resulting in the expression of the Htt exon 1 with expanded 103 CAG polyglutamine (103Q) region. Cells were seeded at 3×104 cells/well on a 24-well plate and transfected with a ratio of 0.8 µg HDG 20 to 2 µL Lipofectamine 2000 (Invitrogen) depending on the desired HDG concentration. After a 4-hour treatment, the transfection media was removed, whole media was added for 1-hour, and then the cells were induced using 5 µM muristerone for 24 hours. The Promega CellTiter-Glo Luminescent cell viability assay was then used. The control cells using only Lipofectamine 2000 were counted and plated at 2×104 cells in at least 6 wells of a 96-well plate. The same volume of cells used in this control at 24-hours, was used in the following treatments at that time point and the remaining 48 and 72-hour time points. After the cells were replated, an equal amount of cell viability substrate was added to each well, according to protocol. After the substrate is added, the plate was placed on a rocker for 2 mins then incubated for 10 mins. Finally, the plate was read 3 times per treatment on a Victor3V 1420 Multilabel counter and analyzed using the Wallac 1420 software.

REFERENCES

The following references are incorporated herein by reference in their entirety for all purposes.

1. Landles C, Bates G P: Huntingtin and the molecular pathogenesis of Huntington's disease. Fourth in molecular medicine review series. *EMBO Rep.* 2004, 5:958-963.
2. DiFiglia M, Sapp E, Chase K O, Davies S W, Bates G P, Vonsattel J P, Aronin N: Aggregation of huntingtin in neuronal intranuclear inclusions and dystrophic neurites in brain. *Science* 1997, 277:1990-1993.
3. Scherzinger E, Sittler A, Schweiger K, Heiser V, Lurz R, Hasenbank R, Bates G P, Lehrach H, Wanker E E: Self-assembly of polyglutamine-containing huntingtin fragments into amyloid-like fibrils: implications for Huntington's disease pathology. *Proc. Natl. Acad. Sci. U.S.A* 1999, 96:4604-4609.
4. Scherzinger E, Lurz R, Turmaine M, Mangiarini L, Hollenbach B, Hasenbank R, Bates G P, Davies S W, Lehrach H, Wanker E E: Huntingtin-encoded polyglutamine expansions form amyloid-like protein aggregates in vitro and in vivo. *Cell* 1997, 90:549-558.
5. Sanchez I, Mahlke C, Yuan J: Pivotal role of oligomerization in expanded polyglutamine neurodegenerative disorders. *Nature* 2003, 421:373-379.
6. Slow E J, Graham R K, Osmand A P, Devon R S, Lu G, Deng Y, Pearson J, Vaid K, Bissada N, Wetzel R, Leavitt B R, Hayden M R: Absence of behavioral abnormalities and neurodegeneration in vivo despite widespread neuronal huntingtin inclusions. *Proc. Natl. Acad. Sci. U.S.A* 2005, 102:11402-11407.
7. Jing N, Li Y, Xu X, Sha W, Li P, Feng L, Tweardy D J: Targeting Stat3 with G-quartet oligodeoxynucleotides in human cancer cells. *DNA Cell Biol.* 2003, 22:685-696.
8. Jing N, De Clercq E, Rando R F, Pallansch L, Lackman-Smith C, Lee S, Hogan M E: Stability-activity relationships of a family of G-tetrad forming oligonucleotides as potent HIV inhibitors. A basis for anti-HIV drug design. *J. Biol. Chem.* 2000, 275:3421-3430.
9. Mazumder A, Neamati N, Ojwang J O, Sunder S, Rando R F, Pommier Y: Inhibition of the human immunodeficiency virus type 1 integrase by guanosine quartet structures. *Biochemistry* 1996, 35:13762-13771.
10. Sen D, Gilbert W: A sodium-potassium switch in the formation of four-stranded G4-DNA. *Nature* 1990, 344:410-414.
11. Arrasate M, Mitra S, Schweitzer E S, Segal M R, Finkbeiner S: Inclusion body formation reduces levels of mutant huntingtin and the risk of neuronal death. *Nature* 2004, 431:805-810.
12. Kim M, Lee H S, Laforet G, McIntyre C, Martin E J, Chang P, Kim T W, Williams M, Reddy P H, Tagle D, Boyce F M, Won L, Heller A, Aronin N, DiFiglia M: Mutant huntingtin expression in clonal striatal cells: dissociation of inclusion formation and neuronal survival by caspase inhibition. *J. Neurosci.* 1999, 19:964-973.
13. Saudou F, Finkbeiner S, Devys D, Greenberg M E: Huntingtin acts in the nucleus to induce apoptosis but death does not correlate with the formation of intranuclear inclusions. *Cell* 1998, 95:55-66.
14. Klement I A, Skinner P J, Kaytor M D, Yi H, Hersch S M, Clark H B, Zoghbi H Y, Orr H T: Ataxin-1 nuclear localization and aggregation: role in polyglutamine-induced disease in SCA1 transgenic mice. *Cell* 1998, 95:41-53.
15. Stenoien D L, Cummings C J, Adams H P, Mancini M G, Patel K, DeMartino G N, Marcelli M, Weigel N L, Mancini M A: Polyglutamine-expanded androgen receptors form aggregates that sequester heat shock proteins, proteasome components and SRC-1, and are suppressed by the HDJ-2 chaperone. *Hum. Mol. Genet.* 1999, 8:731-741.
16. Bowman A B, Yoo S Y, Dantuma N P, Zoghbi H Y: Neuronal dysfunction in a polyglutamine disease model occurs in the absence of ubiquitin-proteasome system impairment and inversely correlates with the degree of nuclear inclusion formation. *Hum. Mol. Genet.* 2005, 14:679-691.
17. Parekh-Olmedo H, Wang J, Gusella J F, Kmiec E B: Modified single-stranded oligonucleotides inhibit aggregate formation and toxicity induced by expanded polyglutamine. *J. Mol. Neurosci.* 2004, 24:257-267.
18. Huang C C, Faber P W, Persichetti F, Mittal V, Vonsattel J P, MacDonald M E, Gusella J F: Amyloid formation by mutant huntingtin: threshold, progressivity and recruitment of normal polyglutamine proteins. *Somat. Cell Mol. Genet.* 1998, 24:217-233.
19. Wang J, Gines S, MacDonald M E, Gusella J F: Reversal of a full-length mutant huntingtin neuronal cell phenotype by chemical inhibitors of polyglutamine-mediated aggregation. *BMC. Neurosci.* 2005, 6:1.

20. Macaya R F, Schultze P, Smith F W, Roe J A, Feigon J: Thrombin-binding DNA aptamer forms a unimolecular quadruplex structure in solution. *Proc. Natl. Acad. Sci. U.S.A* 1993, 90:3745-3749.
21. Heiser V, Scherzinger E, Boeddrich A, Nordhoff E, Lurz R, Schugardt N, Lehrach H, Wanker E E: Inhibition of huntingtin fibrillogenesis by specific antibodies and small molecules: implications for Huntington's disease therapy. *Proc. Natl. Acad. Sci. U.S.A* 2000, 97:6739-6744.
22. Hardin C C, Henderson E, Watson T, Prosser J K: Monovalent cation induced structural transitions in telomeric DNAs: G-DNA folding intermediates. *Biochemistry* 1991, 30:4460-4472.
23. Balagurumoorthy P, Brahmachari S K: Structure and stability of human telomeric sequence. *J. Biol. Chem.* 1994, 269:21858-21869.
24. Balagurumoorthy P, Brahmachari S K, Mohanty D, Bansal M, Sasisekharan V: Hairpin and parallel quartet structures for telomeric sequences. *Nucleic Acids Res.* 1992, 20:4061-4067.
25. Apostol B L, Kazantsev A, Raffioni S, Illes K, Pallos J, Bodai L, Slepko N, Bear J E, Gertler F B, Hersch S, Housman D E, Marsh J L, Thompson L M: A cell-based assay for aggregation inhibitors as therapeutics of polyglutamine-repeat disease and validation in *Drosophila*. *Proc. Natl. Acad. Sci. U.S.A* 2003, 100:5950-5955.
26. Yang W, Dunlap J R, Andrews R B, Wetzel R: Aggregated polyglutamine peptides delivered to nuclei are toxic to mammalian cells. *Hum. Mol. Genet.* 2002, 11:2905-2917.
27. Chen S, Berthelier V, Hamilton J B, O'Nuallain B, Wetzel R: Amyloid-like features of polyglutamine aggregates and their assembly kinetics. *Biochemistry* 2002, 41:7391-7399.
28. Zakian V A: Telomeres: beginning to understand the end. *Science* 1995, 270:1601-1607.
29. Sun D, Thompson B, Cathers B E, Salazar M, Kerwin S M, Trent J O, Jenkins T C, Neidle S, Hurley L H: Inhibition of human telomerase by a G-quadruplex-interactive compound. *J. Med. Chem.* 1997,40:2113-2116.
30. Fedoroff O Y, Salazar M, Han H, Chemeris W V, Kerwin S M, Hurley L H: NMR-Based model of a telomerase-inhibiting compound bound to G-quadruplex DNA. *Biochemistry* 1998, 37:12367-12374.
31. Bates G: Huntingtin aggregation and toxicity in Huntington's disease. *Lancet* 2003, 361:1642-1644.
32. Ross C A, Poirier M A, Wanker E E, Amzel M: Polyglutamine fibrillogenesis: the pathway unfolds. *Proc. Natl. Acad. Sci. U.S.A* 2003, 100:1-3.
33. Dapic V, Abdomerovic V, Marrington R, Peberdy J, Rodger A, Trent J O, Bates P J: Biophysical and biological properties of quadruplex oligodeoxyribonucleotides. *Nucleic Acids Res.* 2003, 31:2097-2107.
34. Jing N, Sha W, Li Y, Xiong W, Tweardy D J. Rational drug design of G-quartet DNA as anti-cancer agents. *Curr Pharm Des.* 2005; 11(22):2841-54. Review.
35. Jing N, Li Y, Xiong W, Sha W, Jing L, Tweardy D J. G-quartet oligonucleotides: a new class of signal transducer and activator of transcription 3 inhibitors that suppresses growth of prostate and breast tumors through induction of apoptosis. *Cancer Res*. Sep. 15, 2004; 64(18): 6603-9.
36. Biyani and Nisigaki, Structural Characterization of Ultra-Stable Higher-Ordered Aggregates Generated by Novel Guanine-rich DNA Sequences. *Gene* 2005; 364: 130-38.

The invention claimed is:

1. A method of inhibiting or reducing the aggregation of polyglutamine-containing proteins associated with polyglutamine diseases comprising: providing an oligonucleotide of from 15 to 50 nucleotides, wherein at least 60% of the nucleotides are guanosine nucleotides; providing a polyglutamine-containing protein or a protein aggregate; and contacting the polyglutamine-containing protein or protein aggregate with an effective amount of the oligonucleotide sufficient to inhibit or reduce protein aggregation.

2. The method of claim 1, wherein the oligonucleotide is capable of forming a stable G-quartet structure.

3. The method of claim 1, wherein the oligonucleotide is from 16 to 26 nucleotides.

4. The method of claim 1, wherein the oligonucleotide is at least one of the oligonucleotides as set forth in SEQ ID NO: 3 or 7.

* * * * *

SEQUENCE LISTING

<160> NUMBER OF SEQ ID NOS: 12

<210> SEQ ID NO 1
<211> LENGTH: 16
<212> TYPE: DNA
<213> ORGANISM: Artificial
<220> FEATURE:
<223> OTHER INFORMATION: Chemically Synthesized

<400> SEQUENCE: 1
gggtgggtgg gtgggt                                                          16

<210> SEQ ID NO 2
<211> LENGTH: 24
<212> TYPE: DNA
<213> ORGANISM: Artificial
<220> FEATURE:
<223> OTHER INFORMATION: Chemically Synthesized

<400> SEQUENCE: 2
gggggtgggg gtgggggtgg gggt                                                 24

<210> SEQ ID NO 3
<211> LENGTH: 20
<212> TYPE: DNA
<213> ORGANISM: Artificial
<220> FEATURE:
<223> OTHER INFORMATION: Chemically Synthesized

<400> SEQUENCE: 3

-continued gggggggggg gggggggggg                                               20

<210> SEQ ID NO 4
<211> LENGTH: 20
<212> TYPE: DNA
<213> ORGANISM: Artificial
<220> FEATURE:
<223> OTHER INFORMATION: Chemically Synthesized

<400> SEQUENCE: 4
gtgtgtgtgt gtgtgtgtgt                                               20

<210> SEQ ID NO 5
<211> LENGTH: 20
<212> TYPE: DNA
<213> ORGANISM: Artificial
<220> FEATURE:
<223> OTHER INFORMATION: Chemically Synthesized

<400> SEQUENCE: 5
ggtggtggtg gtggtggtgg                                               20

<210> SEQ ID NO 6
<211> LENGTH: 20
<212> TYPE: DNA
<213> ORGANISM: Artificial
<220> FEATURE:
<223> OTHER INFORMATION: Chemically Synthesized

<400> SEQUENCE: 6
gggtgggtgg gtgggtgggt                                               20

<210> SEQ ID NO 7
<211> LENGTH: 20
<212> TYPE: DNA
<213> ORGANISM: Artificial
<220> FEATURE:
<223> OTHER INFORMATION: Chemically Synthesized

<400> SEQUENCE: 7 gggggtggg gggtgggggg                                                20

<210> SEQ ID NO 8
<211> LENGTH: 20
<212> TYPE: DNA
<213> ORGANISM: Artificial
<220> FEATURE:
<223> OTHER INFORMATION: Chemically Synthesized

<400> SEQUENCE: 8
cccccccccc cccccccccc                                               20

<210> SEQ ID NO 9
<211> LENGTH: 20
<212> TYPE: DNA
<213> ORGANISM: Artificial
<220> FEATURE:
<223> OTHER INFORMATION: Chemically Synthesized

<400> SEQUENCE: 9
aaaaaaaaaa aaaaaaaaaa                                               20

<210> SEQ ID NO 10
<211> LENGTH: 20
<212> TYPE: DNA

```
<213> ORGANISM: Artificial
<220> FEATURE:
<223> OTHER INFORMATION: Chemically Synthesized

<400> SEQUENCE: 10
tttttttttt tttttttttt                                              20

<210> SEQ ID NO 11
<211> LENGTH: 26
<212> TYPE: DNA
<213> ORGANISM: Artificial
<220> FEATURE:
<223> OTHER INFORMATION: Chemically Synthesized

<400> SEQUENCE: 11
ggtggtggtg gttgtggtgg tggtgg                                       26

<210> SEQ ID NO 12
<211> LENGTH: 29
<212> TYPE: DNA
<213> ORGANISM: Artificial
<220> FEATURE:
<223> OTHER INFORMATION: Chemically Synthesized

<400> SEQUENCE: 12
tttggtggtg gtggttgtgg tggtggtgg                                    29
```